United States Patent
Ward et al.

(10) Patent No.: US 11,186,567 B2
(45) Date of Patent: Nov. 30, 2021

(54) AMPA RECEPTOR POTENTIATORS

(71) Applicant: UNIVERSITY COLLEGE CARDIFF CONSULTANTS LIMITED, Cardiff (GB)

(72) Inventors: Simon Ward, South Glamorgan (GB); Paul Beswick, Cambridgeshire (GB); Lewis Pennicott, Sussex (GB); Tristan Reuillon, Sussex (GB)

(73) Assignee: University College Cardiff Consultants Limited, Cardiff (GB)

( * ) Notice: Subject to any disclaimer, the term of this patent is extended or adjusted under 35 U.S.C. 154(b) by 0 days.

(21) Appl. No.: 16/482,791

(22) PCT Filed: Feb. 9, 2018

(86) PCT No.: PCT/GB2018/050370
§ 371 (c)(1),
(2) Date: Aug. 1, 2019

(87) PCT Pub. No.: WO2018/146486
PCT Pub. Date: Aug. 16, 2018

(65) Prior Publication Data
US 2021/0139463 A1 May 13, 2021

(30) Foreign Application Priority Data
Feb. 10, 2017 (GB) .................... 1702221

(51) Int. Cl.
*C07D 403/10* (2006.01)
*A61K 31/4155* (2006.01)
*A61K 45/06* (2006.01)

(52) U.S. Cl.
CPC ........ *C07D 403/10* (2013.01); *A61K 31/4155* (2013.01); *A61K 45/06* (2013.01)

(58) Field of Classification Search
CPC ... C07D 403/10; A61K 31/4155; A61K 45/06
USPC ...................................... 514/406
See application file for complete search history.

(56) References Cited

U.S. PATENT DOCUMENTS

| 6,284,785 | B1 | 9/2001 | Mutel et al. |
| 7,998,999 | B2 | 8/2011 | Wallace et al. |
| 2009/0275751 | A1 | 11/2009 | Nagato et al. |
| 2021/0139463 | A1 | 5/2021 | Ward et al. |

FOREIGN PATENT DOCUMENTS

| WO | WO-2004/046137 | 6/2004 |
| WO | WO-2006/109056 | 10/2006 |
| WO | WO-2007/107539 | 9/2007 |
| WO | WO-2008/053031 | 5/2008 |
| WO | 2008148836 A1 | 12/2008 |
| WO | WO-2008/148832 | 12/2008 |
| WO | WO-2008/148836 | 12/2008 |
| WO | WO-2009/017664 | 2/2009 |
| WO | WO-2009/038752 | 3/2009 |
| WO | WO-2009/053448 | 4/2009 |
| WO | WO-2009/062930 | 5/2009 |
| WO | WO-2009/134392 | 11/2009 |
| WO | 2009147167 A1 | 12/2009 |
| WO | WO-2009/147167 | 12/2009 |
| WO | WO-2010/063666 | 6/2010 |
| WO | WO-2010/150192 | 12/2010 |
| WO | WO-2011/132051 | 10/2011 |
| WO | WO-2012/120428 | 9/2012 |
| WO | WO-2018/146486 | 8/2018 |
| WO | WO-2019/166822 | 9/2019 |

OTHER PUBLICATIONS

European Patent Office, International Search Report and Written Opinion for PCT/GB2018/050370, dated Mar. 20, 2018, 13 pages.
European Patent Office, International Search Report and Written Opinion for PCT/GB2019/050578, dated Sep. 6, 2019, 10 pages.
Morrow et al., Recent advances in positive allosteric modulators of the AMPA receptor. Current Opinion in Drug Discovery and Development, 2006, 9(5) 571-579.
O'Neill et al. AMPA receptor potentiators as cognitive enhancers. Idrugs 2007;10:185-192.
Quintana et al., The Promise of Intranasal Esketamine as a Novel and Effective Antidepressant, JAMA Psychiatry, 2018, 75(2), 123-124.
Singer, Why Ketamine Helps Fight Depression, MIT Technology Review, Aug. 7, 2007, 3 pages.
Aleksandrova et al., "Antidepressant effects of ketamine and the roles of AMPA glutamate receptors and other mechanisms beyond NMDA receptor antagonism," J. Psychiatry Neurosci., 42(4), pp. 222-229 (2017).
Arai et al., "Effect of the AMPA receptor modulator IDRA 21 on LTP in hippocampal slices," NeuroReport, 7, pp. 2211-2215 (1996).

(Continued)

Primary Examiner — Kristin A Vajda
(74) Attorney, Agent, or Firm — Mintz, Levin, Cohn, Ferris, Glovsky and Popeo, P.C.

(57) ABSTRACT

The invention provides compounds of the formula (I): wherein $R^1$ and $R^2$ are defined in the specification, to pharmaceutical compositions comprising the compounds and the compounds for use as medicaments. The compounds potentiate AMPA receptor function and are expected to be useful in the treatment of central nervous system disorders, for example in the treatment of depressive disorders, mood disorders and cognitive dysfunction associated with neuropsychiatric disorders such as schizophrenia.

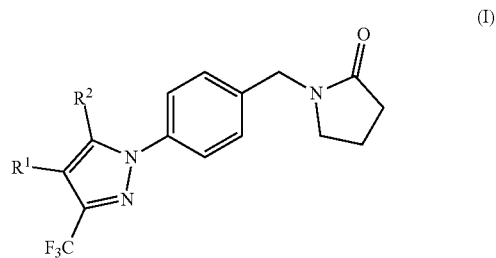

(I)

20 Claims, No Drawings

(56) References Cited

OTHER PUBLICATIONS

Arai et al., "Effects of the Potent Ampakine CX614 on Hippocampal and Recombinant AMPA Receptors: Interactions with Cyclothiazide and GYKI 52466," Mol. Pharmacol., 58(4), pp. 802-813 (2000).
Berman et al., "Antidepressant Effects of Ketamine in Depressed Patients," Biol. Psychiatry, 47, pp. 351-354 (2000).
Bloss et al., "Behavioral and biological effects of chronic S18986, a positive AMPA receptor modulator, during aging," Exp. Neurol., 210, pp. 109-117 (2008).
Bretin et al., "Pharmacological characterisation of S 47445, a novel positive allosteric modulator of AMPA receptors," PLOS ONE, 12(9):e0184429, 28 pages (2017).
Cammarota et al., "Inhibitory Avoidance Training Induces Rapid and Selective Changes in $^3$[H]AMPA Receptor Binding in the Rat Hippocampal Formation," Neurobiol. Learn. Mem., 64, pp. 257-264 (1995).
Dai et al., "A brain-targeted ampakine compound protects against opioid-induced respiratory depression," Eur. J. Pharmacol., 809, pp. 122-129 (2017).
Daly et al., "Efficacy and Safety of Intranasal Esketamine Adjunctive to Oral Antidepressant Therapy in Treatment-Resistant Depression: A Randomized Clinical Trial," JAMA Psychiatry, 75(2), pp. 139-148 (2018).
Derkach et al., "Regulatory mechanisms of AMPA receptors in synaptic plasticity," Nat. Rev. Neurosci., 8(2), pp. 101-113 (2007).
Dicou et al., "Positive allosteric modulators of AMPA receptors are neuroprotective against lesions induced by an NMDA agonist in neonatal mouse brain," Brain Research, 970, pp. 221-225 (2003).
Feng et al., "In Vitro P-glycoprotein Assays to Predict the in Vivo Interactions of P-glycoprotein with Drugs in the Central Nervous System," Drug Metab. Dispos., 36(2), pp. 268-275 (2008).
Field et al., "Targeting glutamate synapses in schizophrenia," Trends Mol. Med., 17(12), pp. 689-698 (2011).
Goffin et al., "7-Phenoxy-Substituted 3,4-Dihydro-2H-1,2,4-benzothiadiazine 1,1-Dioxides as Positive Allosteric Modulators of α-Amino-3-hydroxy-5-methyl-4-isoxazolepropionic Acid (AMPA) Receptors with Nanomolar Potency," J. Med. Chem., 61, pp. 251-264 (2018).
Hampson et al., "Mechanisms underlying cognitive enhancement and reversal of cognitive deficits in nonhuman primates by the ampakine CX717," Psychopharmacology, 202(1-3), pp. 355-369 (2009).
Kalivas and Manji, "Neuroplasticity: A new window on therapeutics in neuropsychiatric disease," Neuropsychopharmacology, 33, p. 2 (2008).
Liu et al., "A single fear-inducing stimulus induces a transcription-dependent switch in synaptic AMPAR phenotype," Nature Neuroscience, 13(2), 223-231, 11 pages (2010).
Löscher et al. "The role of technical, biological and pharmacological factors in the laboratory evaluation of anticonvulsant drugs. II. Maximal electroshock seizure models," Epilepsy Res., 8, pp. 79-94 (1991).

Malinow et al., "AMPA Receptor Trafficking and Synaptic Plasticity," Annual Review of Neuroscience, 25, pp. 103-126 (2002).
Mellor, "The AMPA receptor as a therapeutic target: current perspectives and emerging possibilities," Future Med. Chem., 2(5), pp. 877-891 (2010).
O'Neill and Witkin, "AMPA Receptor Potentiators: Application for Depression and Parkinson's Disease," Curr. Drug Targets, 8, pp. 603-620 (2007).
Passafaro et al., "Subunit-specific temporal and spatial patterns of AMPA receptor exocytosis in hippocampal neurons," Nat. Neurosci., 4(9), pp. 917-926 (2001).
Quirk and Nisenbaum, "LY404187: A Novel Positive Allosteric Modulator of AMPA Receptors," CNS Drug Rev., 8(3), pp. 255-282 (2002).
Seeburg et al., "Genetic manipulation of key determinants of ion flow in glutamate receptor channels in the mouse," Brain Res., 907, pp. 233-243 (2001).
Seeburg et al., "RNA editing of brain glutamate receptor channels: mechanism and physiology," Brain Res. Rev., 26, pp. 217-229 (1998).
Shaffer et al., "The Discovery and Characterization of the α-Amino-3-hydroxy-5-methyl-4-isoxazolepropionic Acid (AMPA) Receptor Potentiator N-{(3S,4S)-4-[4-(5-Cyano-2-thienyl)phenoxy]tetrahydrofuran-3-yl}propane-2-sulfonamide (PF-04958242)," J. Med. Chem., 58, pp. 4291-4308 (2015).
Simmons et al., "Up-regulating BDNF with an ampakine rescues synaptic plasticity and memory in Huntington's disease knockin mice," Proc. Natl. Acad. Sci. USA, 106(12), pp. 4906-4911 (2009).
Sobolevsky et al., "X-ray structure, symmetry and mechanism of an AMPA-subtype glutamate receptor," Nature, 462, pp. 745-756, 14 pages (2009).
Sommer et al., "RNA Editing in Brain Controls a Determinant of Ion Flow in Glutamate-Gated Channels," Cell, 67, pp. 11-19 (1991).
Stäubli et al., "Centrally active modulators of glutamate receptors facilitate the induction of long-term potentiation in vivo," Proc. Natl. Acad. Sci. USA, 91, pp. 11158-11162 (1994).
Traynelis et al., "Glutamate Receptor Ion Channels: Structure, Regulation, and Function," Pharmacol. Rev., 62(3), pp. 405-496 (2010).
Ward et al., "Challenges for and current status of research into positive modulators of AMPA receptors," British Journal of Pharmacology, 160, pp. 181-190 (2010).
Ward et al., "Integration of Lead Optimization with Crystallography for a Membrane-Bound Ion Channel Target: Discovery of a New Class of AMPA Receptor Positive Allosteric Modulators," J. Med. Chem., 54(1), pp. 78-94 (2011).
Ward et al., "Pharmacological characterization of N-[(2S)-5-(6-fluoro-3-pyridinyl)-2,3-dihydro-1H-inden-2-yl]-2-propanesulfonamide: a novel, clinical AMPA receptor positive allosteric modulator," British Journal of Pharmacology, 174, pp. 370-385 (2017).
Yamada, "Therapeutic potential of positive AMPA receptor modulators in the treatment of neurological disease," Exp. Opin. Invest. Drugs, 9(4), pp. 765-778 (2000).
Zanos et al., "NMDAR inhibition-independent antidepressant actions of ketamine metabolites," Nature, 533, pp. 481-486, 18 pages (2016).

AMPA RECEPTOR POTENTIATORS

CROSS-REFERENCES TO RELATED APPLICATIONS

This application is a U.S. National Phase Application of PCT International Application No. PCT/GB2018/050370, filed Feb. 9, 2018, which is an International Application of and claims the benefit of priority to British Patent Application No. 1702221.1, filed on Feb. 10, 2017, the entire contents of which are herein incorporated by reference.

This invention relates to compounds of the formula (I) defined herein; to pharmaceutical compositions comprising the compounds. More specifically, the invention relates to compounds which are useful as AMPA (α-amino-3-hydroxy-5-methyl-4-isoxazole propionic acid) glutamate receptor modulators. The invention also relates to uses of the compounds and methods of treatment employing the compounds, particularly in the treatment or prevention of diseases or conditions in which potentiation of the AMPA receptor is beneficial, for example in the treatment of neurological or neuropsychiatric disease, particularly the treatment of depressive disorders, mood disorders and cognitive dysfunction associated with neurodegenerative disorders or neuropsychiatric disorders such as schizophrenia. The invention further comprises methods for preparing the compounds and intermediates used in the preparation of the compounds.

BACKGROUND

Glutamate is the major mediator of excitatory neurotransmitter in the mammalian brain, and is involved in rapid point-to-point (synaptic) communication between neurons. The functions of glutamate are mediated via three types of fast acting ion channels; the kainate, AMPA and N-methyl-D-aspartate (NMDA) subtypes; and also by the more modulatory metabotropic G-protein coupled (mGlu1-8) receptors.

AMPA receptors are tetrameric comprising four subunits (GluA1-GluA4) (Traynelis et al., Glutamate receptor ion channels: structure, regulation, and function; Pharmacol. 2010, Rev. 62, 405-496). Functional AMPA receptors can be formed from homo- or hetero-tetramers. Native receptors are almost exclusively heteromeric which leads to a diversity of receptor subunit composition in the human brain.

Studies of the X-ray structure of the membrane-bound channel show that the AMPA receptor comprises (1) an amino terminal domain (ATD), which is involved in the assembly of subunits and is the site of action for a number of molecules that modulate AMPA receptor function; (2) a ligand binding domain (LBD) including two polypeptide segments S1 and S2, which binds glutamate; (3) a transmembrane domain (TMD) containing a pore-forming ion channel; and (4) a C-terminal intracellular domain. In addition to the various subunit permutations, an additional layer of complexity is created by the existence of a number of splice variants (flip and flop variants) and sites for post-translational modification (Seeburg et al.; RNA editing of brain glutamate receptor channels: mechanism and physiology, Brain Res Rev 26: 217-229, 1998). RNA editing results in a positively charged arginine (R) residue replacing the genomically encoded glutamine (Q) in the M2 re-entrant loop of the GluA2 subunit, thereby restricting $Ca^{2+}$ flux through the channel and essentially rendering the receptor permeable to just $Na^+$ and $K^+$, which is deemed crucial for adult synaptic function and plasticity (Sommer et al.; RNA editing in brain controls a determinant of ion flow in glutamate-gated channels; Cell 105: 11-19, 1991; and Seeburg et al.; Genetic manipulation of key determinants of ion flow in glutamate receptor channels in the mouse. Brain Res 907: 233-243., 2001). Extensive structural studies have been carried out on LBD constructs (Sobolevsky et al, 2009, Nature, 462:745-756).

AMPA receptors are the most highly-expressed ionotropic glutamate receptors in the brain and are responsible for the majority of fast synaptic transmission. AMPA receptor mediated cell depolarization leads to calcium influx via NMDA receptors and the induction of synaptic plasticity (Derkach et al., 2007, Nat. Rev. Neurosci., 8:101-113).

Synaptic plasticity is the cellular process that underlies learning and memory. AMPA receptors are actively trafficked into synapses in response to neuronal activation and a functional correlate of this is that they play a crucial role in long-term potentiation, the electrophysiological correlate of synaptic plasticity (Malinow et al. Annual Review of Neuroscience Vol. 25: 103-126, 2002).

Abnormalities in glutamatergic neurotransmissions are associated with a variety of CNS disorders and the alterations in the function of the kainate, AMPA and/or NMDA subtypes of glutamate ion channels have been explored as therapeutic targets. Of these ion channel subtypes, AMPA receptors interact very closely with NMDA receptors and together they are associated with synaptic plasticity.

AMPA modulators can also produce effects on in-vivo electrophysiological measurements such as long-term potentiation, AMPA induced currents and neuronal firing rates (Hampson et al, Psychopharmacology (Berl). 2009 January; 202(1-3):355-69). The observation that AMPA receptor expression increases after learning a behavioural task (Cammarota et al, Neurobiol. Learn. Mem., 1995, 64, 257-264) or after exposure to a single fear-inducing stimulus (Liu et al, Nature neuroscience 2010, 13(2), 223-31) further emphasizes the importance of AMPA receptors in relation to learning, memory and synaptic plasticity.

In view of the critical role of AMPA receptors in the synaptic plasticity that underlies cognition, AMPA receptor modulators are expected to useful in enhancing cognitive function. AMPA receptor modulators may also be useful in the treatment of cognitive dysfunction associated with medical disorders (e.g. cognitive dysfunction associated with psychotic disorders, depressive disorders or neurodegenerative disorders). AMPA receptor modulators may be useful in the treatment of, for example schizophrenia, Alzheimer's disease, bipolar disorder, attention deficit hyperactivity disorder, depression or anxiety, particularly in the treatment of cognitive dysfunction associated with these disorders.

Although potentiation of AMPA receptors has been shown to promote cognition, it has also been found that AMPA potentiation by certain compounds is linked to undesirable convulsant effects and seizures (Yamada Exp. Opin. Investig. Drugs 2000, 9, 765-777). Direct activation of AMPA receptors using receptor agonists increases the risk of overstimulation and the induction of convulsant effects. This has led to research into the development of allosteric (i.e., non-glutamate binding site) AMPA receptor potentiators as a means of enhancing neuroplasticity and thus treating various neuropsychiatric disorders (Kalivas et al., Neuropsychopharmacology, 2008; 33:2).

Positive allosteric modulators (PAMs) of the AMPA receptor (AMPA-PAMs) stabilize the AMPA receptor in its active conformation following glutamate binding resulting in increased synaptic currents, thereby promoting synaptic transmission and plasticity (Mellor. The AMPA receptor as a therapeutic target: current perspectives and emerging possibilities. Future Med. Chem. 2010; 2:877-891; and O'Neill et al. AMPA receptor potentiators as cognitive enhancers. Idrugs 2007; 10:185-192). Positive allosteric modulators (PAMs) are use-dependent drugs and as such only act when endogenous glutamate is released. PAM potentiation of AMPA receptors may therefore reduce the risk of undesirable side effects associated with AMPA potentiation such as convulsions.

AMPA receptor potentiation using PAMs have shown beneficial effects, including increased ligand affinity for the receptor (Arai et al. (1996) Neuroreport. 7: 221 1-5.); reduced receptor desensitization and reduced receptor deactivation (Arai et al. (2000) 58: 802-813); and facilitate the induction of LTP in vivo (Staubli et al. (1994) Proc Natl Acad. Sci 91: 1 1158-1 1162). The efficacy of various AMPA receptor PAMs in pre-clinical and clinical models of psychiatric disorders, such as schizophrenia, are described in (Morrow et al, Current Opinion in Drug Discovery and Development, 2006, 9(5) 571-579).

Around 1% of the population will suffer from schizophrenia at some point in their life. Symptoms such as paranoia and/or hearing voices can be reasonably well treated by existing medications. However, known drugs have little effect on other symptoms of the disease including lack of motivation, impaired social function, and, particularly, impaired cognition. Cognitive dysfunction manifests itself as difficulties with attention, memory and problem solving and result in patents experiencing a "brain fog". These largely untreated symptoms remain a huge barrier to the resumption of a fully functional, "normal" life for affected individuals.

The recognition of the unmet clinical need in schizophrenia triggered the NIH- and FDA sponsored Measurement and Treatment Research to Improve Cognition in Schizophrenia (MATRICS) initiative that mapped out the regulatory path for treatments for the cognitive impairment associated with schizophrenia (CIAS). Most therapeutic approaches to the treatment of cognitive impairment in schizophrenia have focused on the glutamate system aiming to either directly or indirectly increase NMDA receptor function (Field et al., 2011, Trends Mol. Med., 17:689-98). Direct approaches to increasing NMDA receptor function include glycine transporter type 1 (GlyT1) inhibitors (e.g. R1678, Roche). Indirect approaches include mGluR2 positive allosteric modulators (PAMs), mGluR5 PAMs, mGluR2/3 agonists (e.g. pomaglumetad methionil, LY2140023 Lilly), and D-amino acid oxidase inhibitors. However, there remains a need for new therapies which improve cognitive performance in subjects with schizophrenia and other CNS conditions.

Clinical studies have shown that ketamine provides rapid relief from the symptoms of depression, often in a matter of minutes. This finding has generated significant research interest, because conventional anti-depressants such as SSRI's often take weeks or even months to show anti-depressant effects. Initial studies also suggest that ketamine may have the potential to provide potent fast-acting antidepressant effects even in traditionally difficult to treat patients with severe treatment resistant depression (Berman et al.; Antidepressant effects of ketamine in depressed patients; Biol. Psychiatry. 2000; 47(4):351-354). However, ketamine has several side-effects, including hallucinogenic and addictive properties, which would make abuse of the drug likely. It is therefore unlikely that ketamine will be widely adopted as a treatment for depression.

It has recently been found that the antidepressant effects observed with ketamine are attributable to a metabolite of ketamine, (2R,6R)-hydroxynorketamine, and that this metabolite acts as an AMPA receptor potentiator. In mouse models, the metabolite provides rapid anti-depressant-like effects which persist for at least three days (Zanos et al. NMDA receptor inhibition-independent antidepressant actions of a ketamine metabolite. Nature, May 4, 2016).

Accordingly, AMPA receptor potentiators may be useful in the treatment of, for example, depressive disorder (e.g. major depressive disorder, persistent depressive disorder (dysthymia) or substance/medication induced depressive disorders), anxiety or bipolar-disorders. AMPA receptor potentiators may be particularly useful in the treatment of treatment resistant depressive disorders, for example in the treatment of depression that is resistant to conventional anti-depressant therapies including, but not limited to, tricyclic antidepressants, MAOIs and/or SSRIs.

S47445 is a tricyclic AMPA-PAM of the formula:

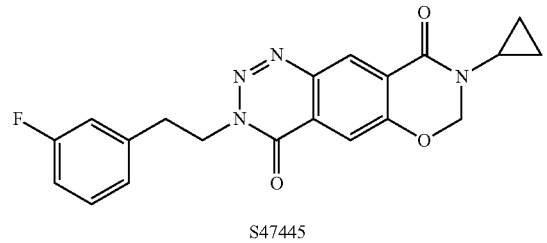 [SMILES: O=C1c2cc3nnn(CCc4cccc(F)c4)c(=O)c3cc2OCN1C1CC1]

S47445

S47445 is described to be a selective AMPA-PAM and shows pro-cognitive effects in rodent models as well as providing neuroprotective effects. The compound is stated to be in clinical trials for the treatment of major depressive disorder and Alzheimer's disease (Bretin et al.; Pharmacological characterisation of S 47445, a novel positive allosteric modulator of AMPA receptors; PLoS ONE. 2017; 12(9)).

Goffin et al. describe certain 7-phenoxy-substituted 3,4-dihydro-2H-1,2,4-benzothiadiazine 1,1-dioxides as AMPA-PAMs (J. Med. Chem., 2018, 61 (1), pp 251-264).

WO2009/147167 discloses certain indane derivatives which are described as potentiators of AMPA receptors.

WO2007/107539, WO2008/053031, WO2008/148832, WO2008/148836 and Ward et al., British Journal of Pharmacology; 160 181-190, 2010; and Ward et al., J. Med. Chem. 2011, 54(1), 78-94 disclose certain compounds, including pyrazole derivatives, as potentiators of AMPA receptors.

WO2010/150192 describes certain isopropylsulphonamide derivatives as potentiators of AMPA receptors. This patent application discloses the compound PF-4958242 as example 4. It has been reported that PF-4958242 provided a relatively narrow therapeutic window between the pro-cognitive effects and pro-convulsant activity (J. Med Chem 2015, 58 (10), 4291-4308).

There remains a need for compounds which potentiate AMPA receptors to provide a pro-cognitive effect. There is also a need for potentiators of AMPA receptors which have a wide therapeutic window between the desirable pro-cognitive effects and the onset of undesirable side-effects, particularly pro-convulsant activity.

An object of the present invention is to provide compounds which potentiate AMPA receptors. Such compounds may be useful for the treatment of diseases associated with glutamatergic disorders, for example as described herein, including but not limited to the use of the compounds in the treatment of major depressive disorder, bipolar disorders or Alzheimer's disease. The compounds may be useful for enhancing cognitive function and/or synaptic plasticity and/or an imbalance in excitatory/inhibitory neurotransmission, particularly when associated with central nervous system (CNS) disorders. In particular the compounds may be useful in the treatment of neurological or neuropsychiatric disease. More particularly the compounds may be useful for the treatment of cognitive impairment associated with a neurological or neuropsychiatric disease.

BRIEF SUMMARY OF THE DISCLOSURE

In accordance with one aspect of the present inventions there is provided a compound of the formula (I):

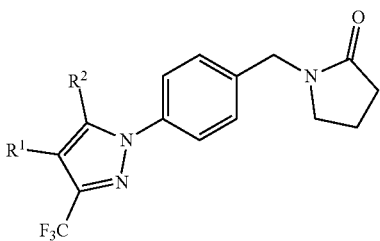

(I)

wherein
$R^1$ is selected from: $C_{1-4}$ alkyl and —$(CH_2)_aOR^4$, wherein a is an integer selected from 1, 2, 3 and 4, and $R^4$ is H or $C_{1-4}$ alkyl;
$R^2$ is selected from: —CN, $C_{1-4}$alkyl, cyclopropyl, —$C_{1-4}$alkylO$C_{1-4}$alkyl and —$(CR^3R^4)_bOH$;
$R^3$ and $R^4$ are each independently selected from H and $C_{1-4}$ alkyl, provided that at least one $R^3$ or $R^4$ in the —$(CR^3R^4)_b$OH group is $C_{1-4}$ alkyl;
b is an integer selected from 1, 2, 3 and 4;
provided that $R^1$ and $R^2$ are not both $C_{1-4}$ alkyl.

In an embodiment $R^1$ is selected from: $C_{1-3}$ alkyl and —$(CH_2)_aOR^4$, wherein a is an integer selected from 1, 2 and 3 (e.g. 1 or 2), and $R^4$ is H or $C_{1-3}$ alkyl.

In an embodiment $R^1$ is selected from: $C_{1-3}$ alkyl, —$CH_2OR^4$ and —$CH_2CH_2OR^4$, wherein $R^4$ is H or methyl.

In an embodiment $R^1$ is selected from: $C_{1-3}$ alkyl, hydroxymethyl and methoxymethyl.

In an embodiment $R^1$ is selected from: methyl, ethyl, hydroxymethyl and methoxymethyl.

In an embodiment $R^1$ is selected from: methyl and hydroxymethyl.

In an embodiment $R^1$ is $C_{1-3}$ alkyl, for example $R^1$ is methyl or ethyl.

In an embodiment $R^1$ is methyl.

In an embodiment $R^1$ is selected from: —$CH_2OH$, —$CH_2CH_2OH$, —$CH_2OCH_3$ and —$CH_2CH_2OCH_3$.

In an embodiment $R^1$ is selected from: —$CH_2OH$ and —$CH_2CH_2OH$.

In an embodiment $R^1$ is —$CH_2OH$.

In an embodiment $R^1$ is selected from: —$CH_2OCH_3$ and —$CH_2CH_2OCH_3$.

In an embodiment a is 1 or 2.
In an embodiment b is 1 or 2.
In an embodiment b is 1 or 2; $R^3$ and $R^4$ are each independently selected from H and $C_{1-2}$ alkyl, provided that at least one $R^3$ or $R^4$ in the —$(CR^3R^4)_b$OH group is $C_{1-2}$ alkyl.

In another embodiment the compound of formula (I) is of the formula (II):

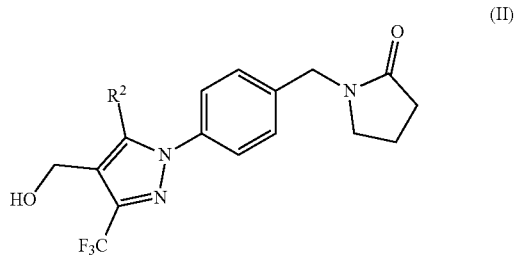

(II)

There are provided compounds of formulae (I) or (II) wherein:
1. $R^2$ is selected from: —CN, $C_{1-3}$alkyl, cyclopropyl, —$C_{1-3}$ alkylO$C_{1-2}$ alkyl and —$(CR^3R^4)_bOH$, wherein b is an integer selected from 1, 2 and 3 (e.g. 1 or 2), and $R^3$ and $R^4$ are each independently selected from H and $C_{1-2}$ alkyl, provided that at least one $R^3$ or $R^4$ in the —$(CR^3R^4)_b$OH group is $C_{1-2}$ alkyl;
2. $R^2$ is selected from: —CN, $C_{1-3}$ alkyl, cyclopropyl, —$C_{1-2}$ alkylO$C_{1-2}$ alkyl, —$CH(R^3)OH$ and —$CH_2CH(R^3)OH$, wherein $R^3$ is methyl or ethyl;
3. $R^2$ is selected from: —CN, $C_{1-3}$ alkyl, —$C_{1-2}$ alkylO$C_{1-2}$ alkyl, —$CH(R^3)OH$ and —$CH_2CH(R^3)OH$, wherein $R^3$ is methyl or ethyl;
4. $R^2$ is selected from: —CN, $C_{1-3}$ alkyl, cyclopropyl, —$C_{1-2}$ alkylOCH$_3$ and —$CH(CH_3)OH$;
5. $R^2$ is selected from: —CN, $C_{1-3}$ alkyl, cyclopropyl, methoxymethyl, —$CH(CH_3)OCH_3$ and —$CH(CH_3)OH$
6. $R^2$ is selected from: —CN, $C_{1-3}$ alkyl and cyclopropyl;
7. $R^2$ is selected from: —CN, methyl, ethyl, isopropyl, cyclopropyl and —$CH(CH_3)OH$;
8. $R^2$ is selected from: —CN, methyl, ethyl, isopropyl and —$CH(CH_3)OH$;
9. $R^2$ is selected from: methyl, ethyl, isopropyl and cyclopropyl; and
10. $R^2$ is selected from: methyl, ethyl and isopropyl.

In another embodiment the compound of formula (I) is of the formula (III):

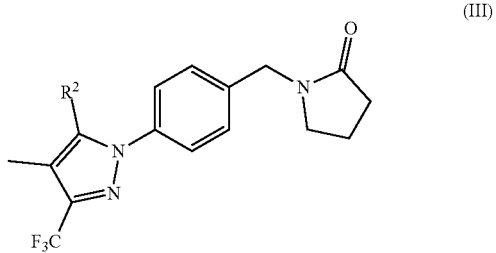

(III)

There are provided compounds of formula (III) wherein:
1. $R^2$ is selected from: —CN, cyclopropyl, —$C_{1-3}$ alkylO$C_{1-2}$ alkyl and —$(CR^3R^4)_bOH$, wherein b is an integer selected from 1, 2 and 3 (e.g. 1 or 2) and $R^3$ and $R^4$ are each independently selected from H and $C_{1-2}$ alkyl, provided that at least one $R^3$ or $R^4$ in the —$(CR^3R^4)_b$OH group is $C_{1-2}$ alkyl; or
2. $R^2$ is selected from: —CN, cyclopropyl, —$C_{1-2}$ alkylO$C_{1-2}$ alkyl, —$CH(R^3)OH$ and —$CH_2CH(R^3)OH$, wherein $R^3$ is methyl or ethyl; or 3. $R^2$ is selected from: —CN, —$C_{1-2}$ alkylO$C_{1-2}$ alkyl, —CH($R^3$)OH and —CH$_2$CH($R^3$)OH, wherein $R^3$ is methyl or ethyl; or
4. $R^2$ is selected from: —CN, cyclopropyl, —$C_{1-2}$ alkylOCH$_3$ and —CH(CH$_3$)OH; or
5. $R^2$ is selected from: —CN, cyclopropyl, —CH(CH$_3$)OH, —CH(CH$_3$)OCH$_3$, methoxymethyl and 2-methoxyethyl; or
6. $R^2$ is selected from: —CN, cyclopropyl, methoxymethyl and —CH(CH$_3$)OH; or
7. $R^2$ is selected from: —CN, methoxymethyl and —CH(CH$_3$)OH.
8. $R^2$ is selected from: methoxymethyl and —CH(CH$_3$)OH.

In one embodiment there is provided a compound of formula (I) wherein
$R^1$ is selected from $C_{1-3}$ alkyl, hydroxymethyl and methoxymethyl; and
$R^2$ is selected from —CN, $C_{1-3}$ alkyl, cyclopropyl, —CH(OH)CH$_3$ and methoxymethyl;
provided that when $R^1$ is $C_{1-3}$ alkyl then $R^2$ is not $C_{1-3}$ alkyl or cyclopropyl.

In one embodiment there is provided a compound of formula (I) wherein
$R^1$ is selected from $C_{1-2}$ alkyl and hydroxymethyl; and
$R^2$ is selected from —CN, $C_{1-3}$ alkyl, cyclopropyl, —CH(OH)CH$_3$ and methoxymethyl;
preferably in this embodiment when $R^1$ is $C_{1-2}$ alkyl then $R^2$ is not $C_{1-3}$ alkyl or cyclopropyl.

In another embodiment there is provided a compound of the formula (I) wherein:
$R^1$ is selected from: methyl, hydroxymethyl and methoxymethyl; and
$R^2$ is selected from —CN, methyl, ethyl, n-propyl, isopropyl, cyclopropyl, methoxymethyl and —CH(OH)CH$_3$; provided that when $R^1$ methyl then $R^2$ is not methyl, ethyl, n-propyl, isopropyl or cyclopropyl.

In another embodiment there is provided a compound of the formula (I) wherein:
$R^1$ is selected from: methyl, hydroxymethyl and methoxymethyl; and
$R^2$ is selected from —CN, methyl, ethyl, isopropyl, cyclopropyl, methoxymethyl and —CH(OH)CH$_3$;
provided that when $R^1$ methyl then $R^2$ is not methyl, ethyl, isopropyl or cyclopropyl.

In another embodiment there is provided a compound of the formula (I) wherein
$R^1$ is methyl and $R^2$ is selected from: —CN, methoxymethyl and —CH(OH)CH$_3$; or
$R^1$ is methoxymethyl or hydroxymethyl and $R^2$ is methyl.

In another embodiment there is provided a compound of the formula (I) selected from:

In accordance with another aspect, the present invention provides a compound of the present invention for use as a medicament.

In accordance with another aspect, the present invention provides a pharmaceutical formulation comprising a compound of the present invention and a pharmaceutically acceptable excipient.

In an embodiment the pharmaceutical composition may be a combination product comprising an additional therapeutic agent. The additional therapeutic agent may be one or more agents used in the treatment of a CNS condition, for example a neurological or psychiatric condition, particularly therapeutic agents used for the treatment of psychotic conditions such as schizophrenia and related conditions. The additional therapeutic may be one or more agents used in the treatment of depressive disorders (e.g. major depressive disorders). Additional therapeutic agents that may be used together with the compounds of the invention are set out in the Detailed Description of the invention below.

In accordance with another aspect, there is provided a compound of the present invention for use in the treatment of glutamatergic disorders, especially glutamatergic disorders modulated by an AMPA receptor.

In accordance with another aspect, there is provided a compound of the present invention for use in the treatment of a condition which is modulated by an AMPA receptor.

Also provided are methods of treating a condition which is modulated by an AMPA receptor in a subject in need thereof by administering an effective amount of a compound of the invention to the subject.

Suitably the compound of the invention is for use in the treatment of a condition in which AMPA receptor function is impaired.

The compound of the invention may be for use in the treatment of a condition in which potentiation of an AMPA receptor is beneficial. Accordingly, it may be that the compound of the invention is for use in enhancing synaptic plasticity in a subject. It may be that the compound of the invention is for use in the treatment of an imbalance in excitatory/inhibitory neurotransmission in a subject.

It may be that the compound of the invention is for use in the treatment or prevention of central nervous system (CNS) disorders associated with an alteration in one or more of cognitive function, synaptic plasticity, or an imbalance in excitatory/inhibitory neurotransmission. For example, a compound of the invention may be for use in the treatment of any of the central nervous system (CNS) disorders disclosed herein, including neurological or neuropsychiatric disorders, for example a condition selected from schizophrenia, bipolar disorder, attention-deficit hyperactivity disorder (ADHD), depression, Alzheimer's disease, Huntington's disease, Parkinson's disease, Down syndrome and other neurodevelopmental disorders, motor neuron diseases such as amyotrophic lateral sclerosis, ataxia, respiratory depression and hearing disorders (for example hearing loss and tinnitus). It may be that the compound of the invention is for use in the treatment of obsessive-compulsive disorder, addiction or mood disorders (including major depressive disorders and bipolar disorders). In some embodiments a compound of the invention is for use in the treatment of a depressive disorder, for example the treatment of a depressive disorder that is resistant to conventional anti-depressant therapies. In some embodiments a compound of the invention is for use in the treatment of a depressive disorder or a mood disorder (e.g., a major depressive disorder, an anxiety disorder, a disruptive mood dysregulation disorder, anhedonia or suicidal ideation (suicidal thoughts)).

Also provided is a compound of the invention for use in the alteration of cognitive function, particularly for the enhancement of cognitive function, in a subject. More particularly there is provided a compound of the invention for use in the treatment of a cognitive impairment. Still more particularly there is provided a compound of the invention for use in the treatment of cognitive impairment associated with a disease or a condition. It may be that a compound of the invention is for use in the treatment of cognitive impairment associated with a psychiatric or neurological disorder, for example any of the psychiatric or neurological disorders described herein.

In a particular embodiment there is provided a compound of the invention is for use in the treatment of cognitive dysfunction associated with schizophrenia.

DETAILED DESCRIPTION

Given below are definitions of terms used in this application. Any term not defined herein takes the normal meaning as the skilled person would understand the term.

Reference herein to a "compound of the invention" is a reference to any of the compounds disclosed herein including compounds of the formulae (I), (II) and (Ill).

The term "halo" refers to one of the halogens, group 17 of the periodic table. In particular the term refers to fluorine, chlorine, bromine and iodine. Preferably, the term refers to fluorine or chlorine.

The term "$C_{1-4}$ alkyl" refers to a linear or branched hydrocarbon chain containing 1, 2, 3 or 4 carbon atoms, for example methyl, ethyl, n-propyl, iso-propyl, n-butyl, sec-butyl and tert-butyl.

The term "—$(CH_2)_aOR^A$" refers to a —$(CH_2)_a$— group which carries a terminal $OR^A$ group. For example —$CH_2OH$ (also "hydroxymethyl"), —$CH_2OMe$ (also "methoxymethyl"), —$CH_2CH_2OH$ or —$CH_2CH_2OMe$.

The term "—$C_{1-4}$ alkyl$OC_{1-4}$ alkyl" refers to an alkyl group substituted by a $C_{1-4}$ alkoxy group. —$C_{1-4}$ alkyl$OC_{1-4}$ alkyl groups include, for example —$CH_2OMe$, —$CH_2CH_2OMe$, —$CH(OMe)CH_3$ or —$CH_2CH(OMe)CH_3$.

When $R^2$ is —$(CR^3R^4)_bOH$, the group —$(CR^3R^4)_b$ carries an —OH group (preferably a terminal —OH group) and at least of $R^3$ or $R^4$ is —$C_{1-4}$ alkyl, i.e. the $R^3$ and $R^4$ groups are not all H. Examples of —$(CR^3R^4)_bOH$ include —$CH(CH_3)OH$, —$C(CH_3)_2OH$, —$CH(CH_2CH_3)OH$ and —$CH_2CH(CH_3)OH$.

The invention contemplates pharmaceutically acceptable salts of the compounds of the invention in so far as such compounds may form salts. These may include the acid addition and base salts of the compounds. These may be acid addition and base salts of the compounds. Suitable pharmaceutically acceptable salts are described in for example "Handbook of Pharmaceutical Salts: Properties, Selection, and Use" by Stahl and Wermuth (Wiley-VCH, Weinheim, Germany, 2002). Salts may be formed using well known methods.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J. Pharm. Sci, 64 (8), 1269-1288 by Haleblian (August 1975).

Hereinafter all references to compounds of the invention include references to salts, solvates and complexes thereof and to solvates and complexes or salts thereof.

Compounds of the invention may exist in a single crystal form or in a mixture of crystal forms or they may be amorphous all such forms are encompassed by the present invention. Thus, compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

Certain compounds of the invention are capable of existing in stereoisomeric forms. It will be understood that the invention encompasses the use of all optical isomers of the compounds of the invention. Where a compound has a stereocentre, both (R) and (S) stereoisomers are contemplated by the invention, equally mixtures of stereoisomers or a racemic mixture are contemplated by the present application. Where the compound is a single stereoisomer the compounds may still contain other enantiomers as impurities. Hence a single stereoisomer does not necessarily have an enantiomeric excess (e.e.) of 100% but could have an e.e. or d.e. of about at least 85%. Enantiomerically pure forms are a particular aspect of the invention. Conventional techniques for the preparation/isolation of individual enantiomers when necessary include chiral synthesis from a suitable optically pure precursor or resolution of the racemate (or the racemate of a salt or derivative) using, for example, chiral high pressure liquid chromatography (HPLC).

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, "Stereochemistry of Organic Compounds" by E. L. Eliel and S. H. Wilen (Wiley, 1994).

The present invention also includes all pharmaceutically acceptable isotopically-labelled compounds of formulae (I), (II) or (Ill) wherein one or more atoms are replaced by atoms having the same atomic number, but an atomic mass or mass number different from the atomic mass or mass number most commonly found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, (D) may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labelled compounds can generally be prepared by conventional techniques known to those skilled in the art or by processes analogous to those described using an appropriate isotopically-labelled reagent in place of the non-labelled reagent previously employed.

Prodrugs of the compounds of the invention are also contemplated within the scope of the invention. A prodrug is a compound which acts as a drug precursor which, upon administration to a subject, undergoes conversion by metabolic or other chemical processes to yield a compound of formula (I), (II) or (III). For example, an —OH group may converted to an ester or a carbamate, which upon administration to a subject will undergo conversion back to the free hydroxyl group. Examples of prodrugs and their uses are well known (e.g., Berge et al. (1977) "Pharmaceutical Salts", J. Pharm. Sci. 66:1-19). The prodrugs can be prepared in situ during the final isolation and purification of the compounds, or by separately reacting the purified compound with a suitable esterifying agent.

The terms "treating", or "treatment" refer to any beneficial effect in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, increase enzyme activity, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The therapeutically effective amount of a compound of the invention can be initially estimated from cell culture assays. Target concentrations will be those concentrations of active compound(s) that are capable of achieving the therapeutic effect described herein, as measured using the methods described herein or known in the art.

Therapeutically effective amounts for use in humans can also be determined from animal models using known methods. For example, a dose for humans can be formulated to achieve a concentration that has been found to be effective in animals. The dosage in humans can be adjusted by monitoring compound effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

A prophylactic or therapeutic treatment regimen is suitably one that does not cause substantial toxicity and yet is effective to treat the clinical symptoms demonstrated by the particular patient. This determination of a dosage regimen is generally based upon an assessment of the active compound by considering factors such as compound potency, relative bioavailability, patient body weight, presence and severity of adverse side effects, preferred mode of administration and the toxicity profile of the selected agent.

Without wishing to be bound by theory, the compounds of the invention are thought to potentiate AMPA receptors by acting as positive allosteric modulators (PAMs) of the AMPA receptor. An "allosteric modulator" is an agent which indirectly modulates the effects of an agonist or inverse agonist at a receptor. Allosteric modulators bind to a site distinct from that of the orthosteric agonist binding site. Generally allosteric modulators induce a conformational change within the protein structure of the receptor. A "positive allosteric modulator" (PAM) induces an amplification of the orthosteric agonist's effect, either by enhancing the binding affinity or the functional efficacy of the orthosteric agonist for the target receptor. Accordingly, the compounds of the invention are expected to potentiate the effect of AMPA receptors when endogenous glutamate is released. The compounds of the invention have little or no effect upon channel currents per se and are only able to enhance ion flux through the receptor in the presence of the endogenous glutamate ligand. Accordingly, a compound of the invention may potentiate AMPA receptors by, for example, (i) slowing the rate at which the receptor desensitizes in the continued presence of glutamate; and/or (ii) slowing the rate at which the receptor deactivates after removal of glutamate; and/or (iii) enhancing or prolonging glutamatergic synaptic currents, thereby promoting synaptic transmission and plasticity (e.g. long term potentiation (LTP) of synapses). Preferred compounds potentiate AMPA receptor effects (e.g. enhancing cognition) without significantly corrupting spatial and temporal information.

Compounds of the invention are thought to bind on the twofold axis of the GluA2 ligand binding domain (LBD) dimer which is formed by residues that act as 'hinges' between the two structural domains of each LBD. Modulators binding at this site may act to slow receptor deactivation by stabilizing the clamshell dimer in its closed cleft glutamate bound conformation and/or slow desensitization by stabilizing the dimer interface (Ward et al. British Journal of Pharmacology; 160 181-190, 2010).

Activation of the AMPA receptor by glutamate opens the pore of the ion channel permitting the inward flow of sodium, resulting in the depolarization of the neuronal membrane. This change in the intracellular charge releases the $Mg^{2+}$ cation from the N-methyl-D-aspartate (NMDA) receptor channel, permitting passage of $Ca^{2+}$ through the NMDA receptor pore into the postsynaptic neurone and triggering $Ca^{2+}$-dependent signal transduction cascades, trafficking of extra-synaptic AMPA receptors and high conductance GluA1 homomers to the postsynaptic density, leading to the induction of forms of synaptic plasticity (Passafaro et al.; Subunit-specific temporal and spatial patterns of AMPA receptor exocytosis in hippocampal neurons. Nat Neurosci 4: 917-926, 2001).

The potentiation of AMPA receptors by the compounds of the invention may be assessed by measuring calcium ion influx via AMPA receptors upon exposure of the receptor by glutamate in the presence of a test compound. One such assay is the calcium ion influx assay described in the Examples using cells which express human GluR2 flip (GluA2 flip) AMPA receptor subunits which form functional homotetrameric AMPA receptors. The GluA2 flip sub-units are highly expressed in cortical and sub-cortical brain tissue (Ward et al. 2010, ibid). The Examples show that the compounds of the invention are potent potentiators of AMPA receptors.

The compounds of the invention are expected to enhance cognition. The effect on cognition can be assessed in-vivo using known models of behavioural cognition. For example, a novel object recognition (NOR) model as described in Ennaceur et al. (Behav. Brain Res. 1988, 31, 47-59). The test relies on a rat's natural tendency to explore novelty and involves two trials. In the first (T1) the rat is exposed to two identical objects for a brief period of time (3 min). After a delay (inter trial interval: ITI), the rat is placed back in the chamber with one of the familiar objects it encountered in the first phase and an additional novel object (T2). Rodents typically spend more time exploring the novel object over the familiar object, which is interpreted as reflecting the rodent's memory for the familiar object and its desire to explore a novel object. Because the task relies on the rodent's preference for novelty, it does not require any rule learning and hence no pre-training. Task difficulty can be increased by increasing the delay between T1 and T2. Suitably a compound of the invention has a minimum effective dose in the NOR test of less than 10 mg/kg when administered orally.

Suitably the compounds of the invention provide a wide therapeutic window between the desirable pro-cognitive effects and undesirable side-effects, particularly pro-convulsive effects which may result from over-activation of AMPA receptors.

The potential for a compound to induce convulsive effects may be determined using a variety of models. For example, in-vitro pro-convulsant liability may be assessed using rodent neuronal electrophysiology hippocampus slices to assess potentially convulsive effects of a compound at different concentrations.

Potential pro-convulsant effects in-vivo may be assessed using for example a maximum electroshock threshold (MEST) test. In the MEST test, corneal application of electrical current (CC of approximately 60-70 mA, 0.1 ms duration) in the rat induces tonic and full tonic-clonic seizures. In order to assess the potential of a compound to reduce seizure threshold activity, rats are pre-treated with compound, saline vehicle, or picrotoxin as a positive control 30 min before testing. Models for assessing the convulsant effects of compounds are known and described in, for example Ward et al., J. Med. Chem. 2011, 54(1), 78-94 and Loscher et al. Epilepsy Res. 1991, 8: 79-84.

Suitably the compound of the invention does not show any pro-convulsant activity in the MEST test at doses which are at least 50 times greater than the minimum efficacious dose in the NOR test. For example, no pro-convulsive effects are observed in the MEST test at doses which are greater than 75 times, or preferably greater than 100 times the minimum efficacious dose in the NOR test.

The compounds of the invention suitably have a favourable drug metabolism and pharmacokinetic (DMPK) profile, for example low clearance, high oral bioavailability, high brain penetration and a half-life providing a reasonable duration of action following dosing of the compound.

Suitably the compounds of the invention exhibit a low in-vitro intrinsic clearance (CLi) in the presence of rat, dog and/or human liver microsomes. For example, compounds of the invention preferably have a CLi of less than 100 μL/min/mg in rat and human microsomes. The CLi can be measured using known methods, such as those illustrated in the Examples.

Human P-glycoprotein (P-gp, MDR1) is highly expressed in the blood brain barrier and poses a barrier to brain penetration for P-gp substrates. Compounds with a high P-gp efflux liability may exhibit low penetration of the blood-brain barrier resulting in low, possibly sub-therapeutic, brain concentration of the compound.

Suitably compounds of the invention exhibit an efflux ratio of less than 5, preferably less than 2 when measured in an efflux assay using Madin-Darby canine kidney (MDCK) cell line transfected with human MDR1 as described in Feng et al. (Drug Metabolism and Disposition; The American Society for Pharmacology and Experimental Therapeutics, Vol 36 (2), 2008, 268-275). Compounds of the invention suitably exhibit a high membrane permeability in, for example the PAMPA, assay described in Feng Et al.

The biological properties of the compounds may be assessed using the methods described herein including the Examples. The properties of the compounds may also be assessed using the methodology and screening cascade described in Ward et al. 2010 ibid, for example FIG. 6 therein.

Pharmaceutical Compositions

In accordance with another aspect, the present invention provides a pharmaceutical composition comprising a compound of the invention and a pharmaceutically acceptable excipient.

Conventional procedures for the selection and preparation of suitable pharmaceutical compositions are described in, for example, "Pharmaceuticals—The Science of Dosage Form Designs", M. E. Aulton, Churchill Livingstone, 1988; and Remington: The Science and Practice of Pharmacy, 20th Edition, Lippincott, Williams and Wilkins, 2000.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing). Suitably the compound of the invention is administered orally, for example in the form of a tablet, capsule, granule or powder dosage form.

The compositions of the invention may be obtained by conventional procedures using conventional pharmaceutical excipients, well known in the art. Thus, compositions intended for oral use may contain, for example, one or more fillers, binders, colouring, sweetening, flavouring and/or preservative agents. Pharmaceutical excipients suitable for the preparation of dosage forms are well known, for example as described in the Handbook of Pharmaceutical Excipients, Seventh Edition, Rowe et al.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients, which may vary from about 5 to about 98 percent by weight of the total composition.

Therapeutic Uses and Applications

The Background section herein provides information on the potentiation of AMPA receptors and the potential therapeutic benefits expected to arise therefrom. It is to be understood that this disclosure is also considered to be part of the Detailed Description of the Invention.

The compounds of the invention potentiate AMPA receptors. Accordingly, there is provided a compound of the present invention for use in the treatment of a condition which is modulated by an AMPA receptor.

Suitably the compound of the invention is for use in the treatment of a condition in which AMPA receptor function is impaired. Accordingly, the compound of the invention may be for use in the treatment of a condition in which potentiation of an AMPA receptor is beneficial.

Suitably a compound of the invention is for use in the treatment of a condition in which glutamatergic neurotransmission is dysfunctional. Accordingly, it may be that a compound of the invention is for use in the treatment of a neurological or psychiatric condition associated with glutamate dysfunction. Such glutamatergic disorders are known and include one or more of the conditions described herein.

It may be that the compound of the invention is for use in the treatment of cognitive dysfunction. Cognitive dysfunction may arise as a result of, for example, ageing or as an effect of a disease or condition. In particular a compound of the invention may be for use in the treatment of cognitive dysfunction associated with a neuropsychiatric disease.

It may be that the compound of the invention is for use in the treatment or prevention central nervous system (CNS) disorders associated with an alteration in one or more of cognitive function, synaptic plasticity, or an imbalance in excitatory/inhibitory neurotransmission.

It may be that the compound of the invention is for use in the treatment of cognitive dysfunction associated with a neurological disorder or a neuropsychiatric condition, for example cognitive dysfunction associated with a glutamatergic disorder.

Reference to "cognitive dysfunction" or "cognitive impairment" are used interchangeably herein and refer to a loss or impairment of intellectual functions, including but not limited to one or more of memory, reasoning, problem solving, verbal recall, concentration, attention, speed of processing, executive function, social cognition, verbal learning, visual learning and perception.

A compound of the invention may be for use in the treatment of cognitive impairment, for example impairment of attention, orientation, memory, memory disorders, amnesia, amnesic disorders, age related cognitive impairment, age-associated memory impairment, language function learning disorders and attention disorders.

AMPA receptor modulators have been shown to be beneficial in preclinical models of other diseases, for example, depressive disorders (Quirk et al.: a novel positive allosteric modulator of AMPA receptors; CNS Drug Rev 8: 255-282, 2002; and O'Neill et al., AMPA receptor potentiators: application for depression and Parkinson's disease; Curr Drug Targets 8: 603-620, 2007); Huntington's disease (Simmons et al., Up-regulating BDNF with an ampakine rescues synaptic plasticity and memory in Huntington's disease knockin mice. Proc Natl Acad Sci USA 106: 4906-4911, 2009); stroke (Dicou et al. Positive allosteric modulators of AMPA receptors are neuroprotective against lesions induced by an NMDA agonist in neonatal mouse brain. Br Res 970: 221-225, 2003) and Parkinson's disease (Bloss et al., Behavioural and biological effects of chronic S18986, a positive AMPA receptor modulator, during aging. Exp Neurol 210: 109-117, 2008).

A compound of the invention may be for use in the treatment of one or more of the conditions listed below, for example those listed in the 5 bullet points below. In some embodiments a compound of the invention may be for use in the treatment of one or more of enhancing cognitive function and/or synaptic plasticity and/or an imbalance in excitatory/inhibitory neurotransmission cognitive impairment associated with one or more of the following conditions:

psychosis and psychotic disorders, for example schizophrenia, schizo-affective disorder, schizophreniform diseases, brief reactive psychosis, child onset schizophrenia, "schizophrenia-spectrum" disorders such as schizoid or schizotypal personality disorders, acute psychosis, alcohol psychosis, drug-induced psychosis, autism (including Asperger's disorder and Rett's disorder), delirium, mania (including acute mania), manic depressive psychosis, hallucination, endogenous psychosis, organic psychosyndrome, paranoid and delusional disorders, puerperal psychosis, and psychosis associated with neurodegenerative diseases such as Alzheimer's disease;

substance related disorders; for example, selected from substance abuse substance dependence, substance intoxication, substance withdrawal, alcohol-related disorders, amphetamine related disorders, cannabis related disorders, cocaine related disorders, and nicotine-related disorders, opioid related disorders (for example opioid dependence, opioid abuse, opioid intoxication, opioid withdrawal or opioid induced psychotic disorder);

neurodegenerative diseases, for example selected from Alzheimer's disease; amyotrophic lateral sclerosis; motor neurone disease; motor disorders; Parkinson's disease; dementia in Parkinson's disease; dementia in Huntington's disease; neuroleptic-induced Parkinsonism and tardive dyskinesias; neurodegeneration following stroke, cardiac arrest, pulmonary bypass, traumatic brain injury, spinal cord injury or perinatal hypoxia; and demyelinating diseases such as multiple sclerosis and amyotrophic lateral sclerosis;

depression, for example bipolar depression (including type I and type II), unipolar depression, single or recurrent major depressive episodes with or without psychotic features, catatonic features, melancholic features, atypical features (e.g. lethargy, over-eating/obesity, hypersomnia) or postpartum onset, seasonal affective disorder and dysthymia, depression-related anxiety, psychotic depression; and a disorder selected from post-traumatic stress syndrome, attention deficit disorder, attention deficit hyperactivity disorder, drug-induced disorders (for example disorders induced by phencyclidine, ketamine, opiates, cannabis, amphetamines, dissociative anaesthetics, amphetamine, cocaine and other psychostimulants); Huntingdon's chorea; tardive dyskinesia; dystonia; myoclonus; spasticity; obesity; stroke; sexual dysfunction; sleep disorders including narcolepsy and other conditions resulting from sleep disorder; migraine; trigeminal neuralgia, hearing loss; tinnitus, ocular damage, retinopathy, macular degeneration; and pain (including acute and chronic pain, severe pain, intractable pain, neuropathic pain, and post-traumatic pain).

In embodiments a compound of the invention is for use in the treatment of cognitive impairment associated with any of the conditions listed above. For example a compound of the invention may be for use in the treatment of cognitive impairment associated with or resulting from stroke, Alzheimer's disease, Huntington's disease, Pick disease, Aids-related dementia, Multiinfarct dementia, alcoholic dementia, hypothyroidism-related dementia, and dementia associated to other degenerative disorders such as cerebellar atrophy and amyotrophic lateral sclerosis, delirium, depression trauma, head trauma, aging, neurodegeneration, drug-induced states, neurotoxic agents, autism, Down's syndrome, psychosis, post-electroconvulsive treatment; anxiety disorders (including generalised anxiety disorder, social anxiety disorder, agitation, tension, social or emotional withdrawal in psychotic patients, panic disorder and obsessive compulsive disorder), substance-induced persisting dementia, substance-induced persisting amnesic disorder or substance induced psychotic disorder.

Accordingly one embodiment provides a compound of the invention for use in the treatment of a neurological or neuropsychiatric disease or condition. For example a compound of the invention may be for use in the treatment of Alzheimer's disease, Parkinson's disease, Huntington's disease, Amyotrophic Lateral Sclerosis, schizophrenia, obsessive-compulsive disorder, addiction and mood disorders (including major depressive disorders and bipolar disorder). Particularly the compound of the invention may be for use in the treatment of cognitive dysfunction associated with any such condition.

In a particular embodiment there is provided a compound of the invention for use in the treatment of schizophrenia. For example, a compound of the invention may be for use in the treatment a subtype of schizophrenia selected from paranoid type, disorganised type, catatonic type, undifferentiated type and residual type schizophrenia.

The assessment of the cognitive effects of the compounds in humans suffering from schizophrenia can be assessed using known methods, for example using the MATRICS Consensus Cognitive Battery (MCCB), a standardized battery for use with adults with schizophrenia (Buchanan et al. A summary of the FDA-NIMH-MATRICS workshop on clinical trial design for neurocognitive drugs for schizophrenia. Schizophr. Bull. 2005; 31(1):5-19).

Depressive Disorders

As disclosed in the Background section, ketamine has been shown to be effective in the treatment of depression and that the effects of ketamine are attributable to AMPA receptor potentiation by a metabolite of ketamine. Accordingly, compounds of the invention are expected to be useful in the treatment of depressive disorders, particularly major depressive disorders.

Major depressive disorder (MDD) (also known as clinical depression, major depression, unipolar depression, unipolar disorder or recurrent depression) is defined in the International Statistical Classification of Diseases and Related Health Problems (ICD-10) as a mental disorder characterized by a pervasive and persistent low mood that is accompanied by low self-esteem and by a loss of interest or pleasure in normally enjoyable activities. Depressive disorders also include milder forms of depression, including for example mood-disorders. The depressive disorder may be a hereditary depressive disorder and/or a depressive disorder induced by reaction to environmental or biological stress factors, for example, acute life events, childhood exposure to adversity or stress caused by the signs or symptoms of a medical condition, for example depression that arises from pain in a subject. Depressive disorders may also be associated with or caused by other medical conditions, for example, psychotic disorders, cognitive disorders, eating disorders, anxiety disorders or personality disorders. The depressive disorder may be an acute depressive disorder, a recurrent depressive disorder or a chronic depressive disorder.

In embodiments a compound of the invention is for use in the treatment of a depressive disorder selected from major depressive disorder, dysthymic disorder (persistent depressive disorder), atypical depression, melancholic depression, psychotic depression, catatonic depression, postpartum depression (PPD), premenstrual syndrome, premenstrual dysphoric disorder (PMDD), seasonal affective disorder (SAD), double depression, depressive personality disorder (DPD), recurrent brief depression (RBD), minor depressive disorder, bipolar disorder, bipolar depression, substance/medication-induced depressive disorder (including alcohol-induced and benzodiazepine-induced), post-schizophrenic depression and a depressive disorder caused by or associated with another medical condition (e.g. depressions caused by or associated with a dementia, metabolic disorder, multiple sclerosis, cancer, chronic pain, chemotherapy and/or chronic stress. In some embodiments a compound of the invention is for use in the treatment of a depressive disorder which has an associated anxious component or anxiety disorder. For example, the treatment of a depressive disorder described herein with an associated anxiety disorder as described herein (e.g. selected from a panic disorder, panic disorder with agoraphobia, a social phobia, a specific phobia (e.g. an animal or environmental phobia), post-traumatic distress disorder, an acute stress disorder, an obsessive compulsive disorder (OCD) and panic attacks).

In some embodiments a compound of the invention is for use in the treatment of a mood disorder. Mood disorders are conditions in which a patient's mood changes to depression (often with associated anxiety) and/or to elation. The mood disorders may be acute or recurrent and are often triggered by stressful events or situations. Examples of mood disorders include, manic episodes (e.g. hypomania, mania with psychotic symptoms or mania without psychotic symptoms); a bipolar affective disorder (e.g. manic depression or a manic depressive illness, psychosis or reaction); a depressive episode (e.g. mild, moderate or severe depressive episode); a recurrent depressive disorder; a persistent mood disorders (e.g. cyclothymia or dysthymia); or anhedonia.

Various symptoms are associated with depressive disorders and mood disorders such as MDD, for example, persistent anxious or sad feelings, feelings of helplessness, hopelessness, pessimism, worthlessness, low energy, restlessness, irritability, fatigue, loss of interest in pleasurable activities or hobbies, excessive sleeping, overeating, appetite loss, insomnia, thoughts of suicide, and suicide attempts. The presence, severity, frequency, and duration of these symptoms vary on a case to case basis. In some embodiments, a patient may have at least one, at least two, at least three, at least four, or at least five of these symptoms.

The effect of a compound of the invention on a depressive disorder or mood disorder may be assessed using known methods. For example, an improvement in a patient's symptoms using a suitable clinical scoring or rating system such as a depression symptoms rating scale. Reference to a "depression symptoms rating scale" refers to any one of a number of standardized questionnaires, clinical instruments, or symptom inventories utilized to measure symptoms and symptom severity in depressive disorders. Such rating scales are often used in clinical studies to define treatment outcomes, based on changes from the study's entry point(s) to endpoint(s). Examples of depression symptoms rating scales include, but are not limited to, The Quick Inventory of Depressive-Symptomatology Self-Report (QIDS-SRi6), the 17-Item Hamilton Rating Scale of Depression (HRSDn), the 30-Item Inventory of Depressive Symptomatology (IDS-C30), The Montgomery-Åsberg Depression Rating Scale (MADRS), or The Beck's Depression Scale Inventory. Such ratings scales may involve patient self-report or be clinician rated.

Generally, a 50% or greater reduction in a depression ratings scale score over the course of a clinical trial (starting point to endpoint) is often considered to be a favorable response for most depression symptoms rating scales, although lower % reductions may provide a benefit and are contemplated herein. Generally, "remission" in clinical studies of depression refers to achieving at, or below, a particular numerical rating score on a depression symptoms rating scale (for instance, less than or equal to 7 on the HRSD17; or less than or equal to 5 on the QIDS-SRie; or less than or equal to 10 on the MADRS).

In some embodiments, a compound of the invention is for use in the treatment of a depressive condition or mood disorder (e.g. as described herein), wherein the compound provides a rapid effect on the depressive condition or mood disorder. For example, wherein the compound of the invention provides a clinically meaningful effect on the condition or disorder within 1, 2, 3, 4, 6, 8, 12, 24 or 36 hours after administration of the compound to a subject. The clinical effect of the compound may be assessed using a suitable depression symptoms rating scale.

In some embodiments, a compound of the invention is for use in the treatment of a depressive condition or mood disorder (e.g. as described herein), wherein the compound provides a sustained effect on the condition or disorder following administration of the compound to subject. For example, wherein the compound provides a clinically meaningful effect on the condition or disorder which persists 1 week, 2 weeks, 3 weeks, 4 weeks, 6 weeks, 8 weeks or 12 weeks after administration of the compound to a subject. The clinical effect of the compound may be assessed using a suitable depression symptoms rating scale.

In some embodiments a compound of the invention is for use in the treatment of a treatment resistant depressive disorder. In this embodiment the depressive disorder may be any of the depressive disorders described herein.

Treatment resistant depression (TRD), sometimes referred to as refractory depression, occurs in subjects suffering from a depressive disorder who are resistant to standard pharmacological treatments for the depressive disorder. Examples of standard pharmacological treatments for the depressive disorder including tricyclic antidepressants, monoamine oxidase inhibitors (MAOIs), selective serotonin reuptake inhibitors (SSRIs), serotonin-norepinephrine reuptake inhibitors (SNRIs), ketamine, esketamine or other NMDA modulators, double and triple uptake inhibitors, anxiolytic drugs, atypical anti-depressants and/or anti-psychotic treatments. TRD may also occur in subjects with a depressive disorder who are resistant or non-responsive to non-pharmacological treatments of the depressive disorder (e.g. psychotherapy, electroconvulsive therapy, vagus nerve stimulation and/or transcranial magnetic stimulation).

A treatment resistant-subject may be identified as one who fails to experience alleviation of one or more symptoms of depression (e.g. persistent anxious or sad feelings, feelings of helplessness, hopelessness, pessimism) despite undergoing one or more standard pharmacological or non-pharmacological treatment, such as two, three or four different antidepressant drugs. A treatment-resistant subject may also a subject that does not experience a 50% reduction in depressive symptoms after 2 courses of a standard pharmacological treatment for the depressive disorder.

Suicide Ideation

In some embodiments, a compound of the invention is for use in the treatment of suicide ideation. Suicidal behaviour is one of the leading causes of injury and death worldwide. Suicide ideation, or suicidal thoughts, is often association with or caused by depressive disorders and mood disorders. Accordingly, in certain embodiments there is provided a compound of the invention for use in the treatment or prevention of suicide ideation. It may be that a compound of the invention is for use in the treatment or prevention of suicide ideation in a subject with a depressive disorder or a mood disorder. Examples of depressive conditions or mood disorders are as described herein.

The effects of a compound of the invention may be assessed using a suitable clinical scoring system, for example a suitable suicidal ideation rating scale for the measurement of the severity of suicide ideation. Such suicidal ideation symptoms rating scales include, but are not limited to, Scale for Suicidal Ideation (SSI), the Suicide Status Form (SSF), or the Columbia Suicide Severity Rating Scale (C-SSRS).

Anxiety

In embodiments, a compound of the invention is for use in the treatment of an anxiety disorder. Anxiety is a feeling of apprehension or fear that lingers due to an individual's perception of persistent and unrelenting stress. Anxiety is typically accompanied by various physical symptoms including twitching, trembling, muscle tension, headaches, sweating (e.g., night sweats), dry mouth, or difficulty swallowing. Some people also report dizziness, a rapid or irregular heart rate, shortness of breath, increased rate of respiration, fatigue, nausea, diarrhoea, or frequent need to urinate when they are anxious. Fatigue, irritable mood, sleeping difficulties, decreased concentration, sexual problems, or nightmares are also common. Some people are more sensitive to stress and are thus more likely to develop anxiety disorders. The propensity to succumb to anxiety attacks may be due to genetic predisposition or by previous (e.g. childhood) exposure to certain stresses. Anxiety may also be induced by or associated with medical conditions, for example pain, especially in patients suffering with chronic pain.

Examples of anxiety disorders include separation anxiety disorder, selective mutism, specific phobia, social anxiety disorder (social phobia), panic disorder, panic attack, agoraphobia, post-traumatic stress disorders (PTSD), generalized anxiety disorder, substance/medication-induced anxiety disorder, anxiety disorder due to another medical disorder (e.g. depression), other specified anxiety disorder, or unspecified anxiety disorder. As mentioned above the anxiety disorder may be associated with or be caused by a depressive disorder.

The effect of a compound if the invention in the treatment of an anxiety disorder may be assessed using a suitable anxiety symptom rating scale. Such scales are well-known and include, for example standardized questionnaires, clinical instruments, or symptom inventories utilized to measure symptoms and symptom severity in anxiety. Examples of anxiety symptoms rating scales include, but are not limited to, State-Trait Anxiety Inventory (STAI), the Hamilton Anxiety Rating Scale (HAM-A), the Beck Anxiety Inventory (BAI), and the Hospital Anxiety and Depression Scale-Anxiety (HADS-A). Such ratings scales may involve patient self-reporting or be clinician rated. Generally, a 50% or greater reduction in an anxiety ratings scale score over the course of a clinical trial (starting point to endpoint) is typically considered a favourable response, although lower reductions may also be beneficial and are contemplated.

The effects of a compound of the invention in the treatment of a depressive disorders, mood disorders and anxiety disorders may also be assessed using suitable pre-clinical models. For example, in a forced swim test in rodent; a novelty-suppressed feeding model, a learned helplessness model or a chronic mild stress and social interaction model. Such models are well-known and described in for example, Wang et al The Recent Progress in animal models of depression Prog. Neuro-Psychopharm. Biol Psych. 2017, vol. 77, 99-109; Duman, Vit. Horm. 2010, vol. 82, 1-21 or WO2017/165877.

Respiratory Depression

AMPA receptor potentiators have been found to be useful in the treatment of respiratory depression in preclinical models (Dai et al; A brain-targeted ampakine compound protects against opioid-induced respiratory depression. Eur. J. Pharmacol, 2017, 809:122-9). Accordingly, in another embodiment there is provided a compound of the invention for use in the treatment or prevention of respiratory depression in a subject. For example, a compound of the invention may be for use in the treatment of respiratory depression wherein the respiratory depression is associated with the effect of alcohol, an opiate, an opioid (e.g. fentanyl), or a barbiturate on the subject. In another embodiment a compound of the invention is for use in the treatment or prevention of respiratory depression associated with a condition associated with central sleep apnea, stroke-induced central sleep apnea, obstructive sleep apnea, sleep apnea resulting from Parkinson's disease, congenital hypoventilation syndrome, sudden infant death syndrome, Retts syndrome, Cheney-Stokes respiration, Ondines Curse, spinal muscular atrophy, amyotrophic lateral sclerosis, Prader-Willi's syndrome, spinal cord injury, traumatic brain injury or drowning.

Also provided is a method of treating any of the foregoing conditions in a subject in need thereof by administering an effective amount of a compound of the invention to the subject.

Also provided in the use of a compound of the invention for the manufacture of a medicament for the any of the foregoing conditions.

An effective amount of a compound of the present invention for use in therapy of a condition is an amount sufficient to symptomatically relieve in a subject, particularly a human, the symptoms of the condition or to slow the progression of the condition.

Reference to a "subject" or "patient" herein refers to, for example a warm-blooded mammal, for example a human, non-human primate, cow, horse, pig, goat, sheep, dog, cat, rabbit, mice or rat. Preferably the subject is a human.

The size of the dose for therapeutic or prophylactic purposes of a compound of the invention will naturally vary according to the nature and severity of the conditions, the age and sex of the animal or patient and the route of administration, according to well-known principles of medicine.

In using a compound of the invention for therapeutic or prophylactic purposes it will generally be administered so that a daily dose in the range, for example, a daily dose selected from 0.001 mg/kg to 20 mg/kg, 0.005 mg/kg to 15 mg/kg or 0.01 mg/kg to 10 mg/kg body weight is received, given if required in divided doses. In general lower doses will be administered when a parenteral route is employed. Thus, for example, for intravenous or intraperitoneal administration, a dose in the range, for example, 0.001 mg/kg to 1 mg/kg body weight will generally be used. The daily dose administered orally may be, for example a total daily dose selected from 0.1 mg to 1000 mg, 0.5 mg to 1000 mg, 1 mg to 500 mg or 1 mg to 250 mg. Typically, unit dosage forms will contain about 0.5 mg to 1000 mg, for example 0.5 mg to 500 mg of a compound of this invention.

Combinations

The compound of the invention can be administered alone or can be co-administered together with another therapeutic agent to a subject. The compounds of the invention can be used in co-administered with one or more other active drugs known to be useful in treating a disease (e.g. a drug useful in the treatment of one of the diseases or conditions described herein such as a CNS condition).

By "co-administer" it is meant that a compound of the invention is administered at the same time, prior to, or after the administration of one or more additional therapeutic agent. Co-administration is intended to include simultaneous or sequential administration of the compound and the additional therapeutic agent. Thus, the compound of the invention can be combined, when desired, with other therapeutic agents. For simultaneous administration, the compound of the invention and the therapeutic agent may comprise a single pharmaceutical composition. Alternatively, the compound of the invention and the additional therapeutic agent may be comprised in two separate pharmaceutical compositions, which may be administered to the subject simultaneously or sequentially. The compound of the invention and the one or more additional therapeutic agent may be administered to the subject using the same route of administration or by different routes of administration. For example, the compound of the invention and additional therapeutic agent may be administered orally as a single pharmaceutical composition or as two separate compositions. Alternatively, the compound of the invention may be administered to the subject orally and the therapeutic agent may be administered by a different route of administration, e.g. parenterally. The administrations to the subject may occur substantially simultaneously or sequentially.

Co-administration includes administering one active agent within 0.5, 1, 2, 4, 6, 8, 10, 12, 16, 20, 24, 48 hours or 1 week of a second active agent. Co-administration includes administering two active agents simultaneously, approximately simultaneously (e.g., within about 1, 5, 10, 15, 20, or 30 minutes of each other), or sequentially in any order.

Additional Therapeutic Agent

The additional therapeutic agent may be any therapeutic agent suitable for use in the treatment or prophylaxis of any of the conditions described herein. For example, when the compound of the invention is for use in the treatment of a neurological, psychiatric condition, depressive disorder or mood disorder, the compound of the invention may be co-administered with one or more additional therapeutic agents selected from include antidepressants, antipsychotics, Alzheimer's drugs and anti-anxiety agents.

Accordingly, a compound of the invention may be co-administered with one or more additional therapeutic agents selected from:

typical antipsychotics, for example chlorpromazine, thioridazine, mesoridazine, fluphenazine, perphenazine, prochlorperazine, trifluoperazine, thiothixine, haloperidol, molindone or loxapine;

atypical antipsychotics, for example clozapine, olanzapine, risperidone, quetiapine, aripiprazole, ziprasidone, amisulpride, ziprasidone, paliperidone or bifeprunox;

anticholinergics, for example benztropine, biperiden, procyclidine or trihexyphenidyl; nicotine acetylcholine agonists, for example ispronicline, varenicline and MEM 3454; cholinesterase inhibitors, for example donepezil and galantamine antihistamines, for example diphenhydramine;

dopaminergics, for example amantadine;

serotonin reuptake inhibitors, for example citalopram, escitalopram, fluoxetine, fluvoxamine, paroxetine, sertraline or venlafaxine;

dual serotonin/noradrenaline reuptake inhibitors (SNRIs), for example venlafaxine, desvenlafaxine, duloxetine, milnacipran or levomilnacipran;

triple reuptake inhibitors (serotonin, norepinephrine, dopamine reuptake inhibitors, SNDRIs)), for example, mazindol, nefazodone or sibutramine; noradrenaline (norepinephrine) reuptake inhibitors, for example reboxetine;

NK-1 receptor antagonists, for example aprepitant or maropitant, corticotropin releasing factor (CRF) antagonists, α-adrenoreceptor antagonists;

tricyclic antidepressants, for example amitriptyline, clomipramine, imipramine, maprotiline, nortriptyline or trimipramine, doxepin, trimipramine, dothiepin, butriptyline, iprindole, lofepramine, nortriptyline, protriptyline, amoxapine or desipramine;

monoamine oxidase inhibitors, for example isocarboxazid, moclobemide, phenelzine, selegiline, or tranylcypromine;

atypical anti-depressants, for example bupropion, lithium, nefazodone, trazodone or viloxazine;

other antidepressants, for example bupropion, mianserin, mirtazapine or trazodone;

anxiolytics, for example benzodiazepines (e.g. alprazolam or lorazepam and others below), barbiturates (e.g. secobarbital, mephobarbital, pentobarbital, butabarbital, phenobarbital, or amobarbital);

cognitive enhancers, for example cholinesterase inhibitors (such as tacrine, donepezil, rivastigmine or galantamine;

stimulants, for example methylphenidate, amphetamine formulations or pemoline;

mood stabilisers, for example lithium, sodium valproate, valproic acid, divalproex, carbamazepine, lamotrigine, gabapentin, topiramate or tiagabine;

NMDA receptor antagonists, for example memantine, ketamine and esketamine;

benzodiazepines, for example alprazolam, chlordiazepoxide, clonazepam, chlorazepate, diazepam, halazepam, lorazepam, oxazepam or prazepam; and 5-HT1A receptor agonists or antagonists, for example buspirone, flesinoxan, gepirone and ipsapirone.

According to another aspect of the invention there is provided a compound of the invention and another therapeutic agent for use in the conjoint treatment of a condition which is modulated by an AMPA receptor.

Co-administration of a compound of the invention with another therapeutic agent may be beneficial in preventing or reducing negative side effects associated with the other therapeutic agent. For example, certain therapeutic agents may affect cognitive function in a subject. Accordingly, a further aspect of the invention provides a compound of the invention for use in the treatment of cognitive dysfunction resulting from the administration of another therapeutic agent to a subject.

In these last two embodiments the therapeutic agent may be any of the therapeutic agents other than the compound of the invention described herein, for example an anti-psychotic agent.

In a particular embodiment there is provided a compound of the invention and another therapeutic agent for use in the conjoint treatment of schizophrenia, wherein the other therapeutic agent is a typical antipsychotic (for example chlorpromazine, thioridazine, mesoridazine, fluphenazine, perphenazine, prochlorperazine, trifluoperazine, thiothixine, haloperidol, molindone or loxapine) or an atypical antipsychotic (for example clozapine, olanzapine, risperidone, quetiapine, aripiprazole, ziprasidone, amisulpride, ziprasidone, paliperidone, bifeprunox or talnetant). In this embodiment the conjoined treatment provides a treatment of cognitive impairment associated with schizophrenia.

In another embodiment there is provided a compound of the invention and an anti-depressant for use in the conjoint treatment of a depressive condition (e.g. a major depressive disorder). The anti-depressant may be any anti-depressant other than an AMPA receptor modulator of the invention. For example, a compound of the invention may be for use with an anti-depressant in the conjoined treatment of a depressive disorder, wherein the anti-depressant is selected from a tricyclic antidepressant, a monoamine oxidase inhibitor, a selective serotonin reuptake inhibitor, a serotonin-norepinephrine reuptake inhibitor, an NMDA modulator, a double or triple uptake inhibitor, an anxiolytic drug and an atypical anti-depressant.

Also contemplated is a compound of the invention and a non-pharmacological treatment of a depressive condition for use in the conjoint treatment of a depressive condition (e.g. a major depressive disorder). The non-pharmacological treatment of a depressive condition may be, for example psychotherapy, electroconvulsive therapy, vagus nerve stimulation and/or transcranial magnetic stimulation)

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Synthesis

The skilled person will appreciate that adaptation of methods known in the art could be applied in the manufacture of the compounds of the present invention.

For example, the skilled person will be immediately familiar with standard textbooks such as "Comprehensive Organic Transformations—A Guide to Functional Group Transformations", RC Larock, Wiley-VCH (1999 or later editions), "March's Advanced Organic Chemistry—Reactions, Mechanisms and Structure", MB Smith, J. March, Wiley, (5th edition or later) "Advanced Organic Chemistry, Part B, Reactions and Synthesis", F A Carey, R J Sundberg, Kluwer Academic/Plenum Publications, (2001 or later editions), "Organic Synthesis—The Disconnection Approach", S Warren (Wiley), (1982 or later editions), "Designing Organic Syntheses" S Warren (Wiley) (1983 or later editions), "Guidebook To Organic Synthesis" RK Mackie and DM Smith (Longman) (1982 or later editions), etc., and the references therein as a guide.

The skilled chemist will exercise judgement and skill as to the most efficient sequence of reactions for synthesis of a given target compound and will employ protecting groups as necessary. This will depend inter alia on factors such as the nature of other functional groups present in a particular substrate. Clearly, the type of chemistry involved will influence the choice of reagent that is used in the said synthetic steps, the need, and type, of protecting groups that are employed, and the sequence for accomplishing the protection/deprotection steps. These and other reaction parameters will be evident to the skilled person by reference to standard textbooks and to the examples provided herein.

Sensitive functional groups may need to be protected and deprotected during synthesis of a compound of the invention. This may be achieved by conventional methods, for example as described in "Protective Groups in Organic Synthesis" by TW Greene and PGM Wuts, John Wiley & Sons Inc (1999), and references therein.

Compounds of the formula (I) may be prepared by coupling a compound of the formula (IV) with a compound of formula (V) under Ullmann conditions:

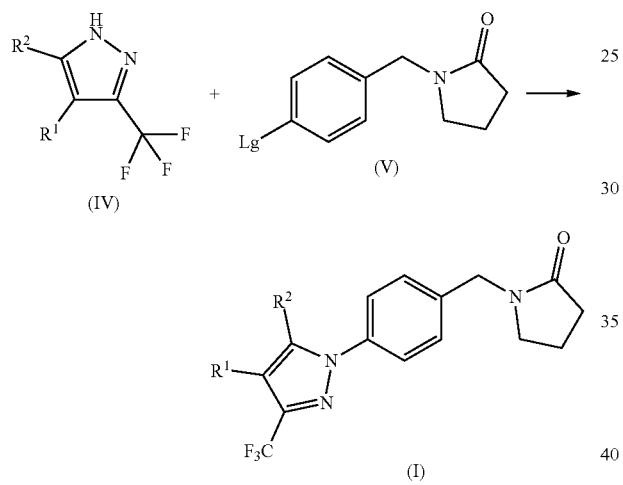

wherein Lg is a suitable leaving group, for example iodo. The reaction is suitably performed in the presence of a base, for example potassium carbonate or caesium carbonate, copper (I) iodide and N,N-dimethylglycine in a suitable solvent, for example dimethylsulfoxide. The reaction is suitably performed at an elevated temperature, for example between about 100° C. to 180° C., suitably at about 130° C.

Compounds of the invention may be prepared according to the following reaction schemes:

Scheme 1

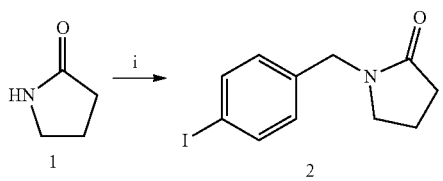

Scheme 1: Reagents and conditions: (i) a) NaH (60% dispersion in mineral oil), DMF, 0° C., 30 min; b) 1-(bromomethyl)-4-iodo-benzene, 0° C., to RT, 18 h, 91%.

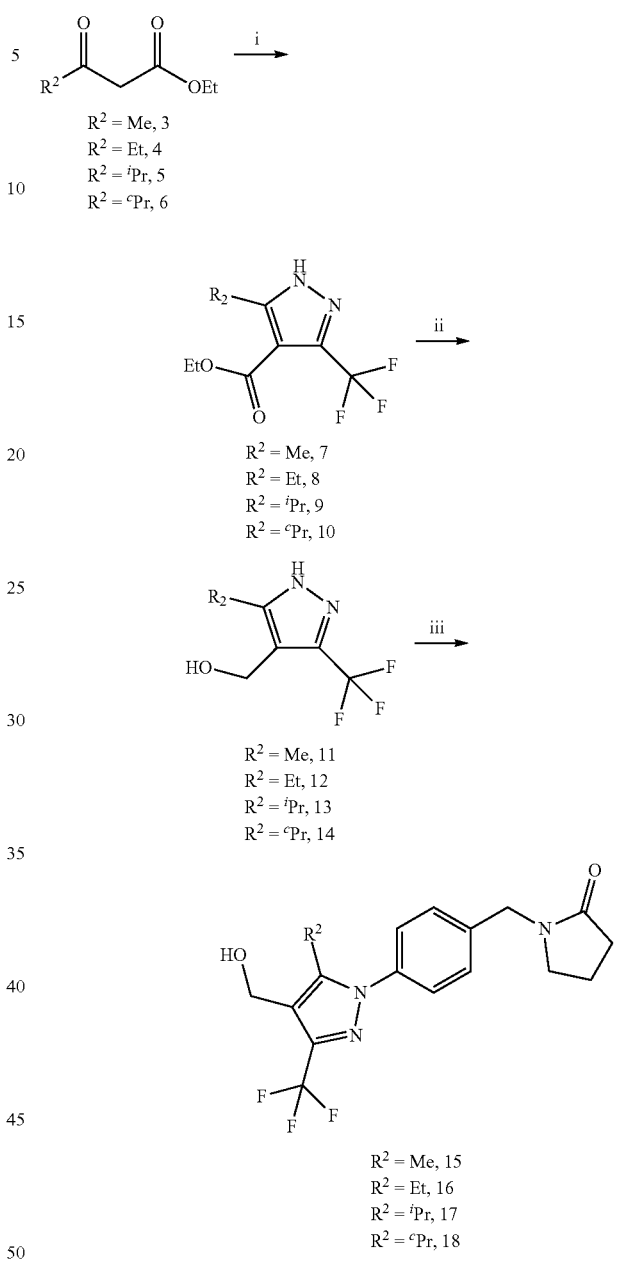

Scheme 2: Reagents and conditions: (i) a) MgCl$_2$, pyridine, trifluoroacetic anhydride, DCM, 0° C. to RT, 18 h; b) hydrazine monohydrate, EtOH, 78° C., 18 h, (R$^2$ = Me, 22%; R$^2$ = Et, 15%; R$^2$ = $^i$Pr, 42%; R$^2$ = $^c$Pr, 3%); (ii) LiAlH$_4$, THF, 0° C. to RT, 24 h, (R$^2$ = Me, 99%; R$^2$ = Et, 95%; R$^2$ = $^i$Pr, 94%; R$^2$ = $^c$Pr, 73%); (iii) 1-[(4-iodophenyl)methyl]pyrrolidin-2-one (2), N,N-dimethylglycine, copper(I) oxide, caesium carbonate, DMSO, 130° C., 18 h, (R$^2$ = Me, 77%; R$^2$ = Et, 70%; R$^2$ = $^i$Pr, 66%; R$^2$ = $^c$Pr, 63%).

Scheme 3

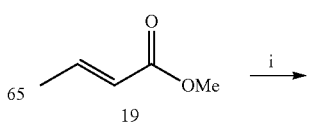

29
-continued

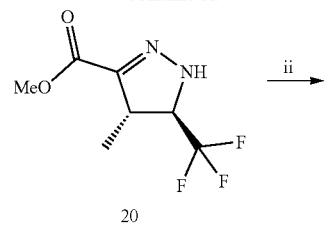
20

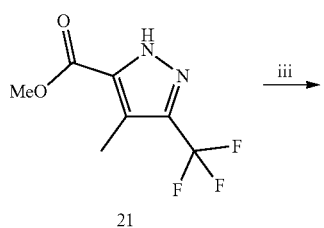
21

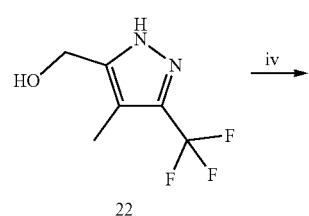
22

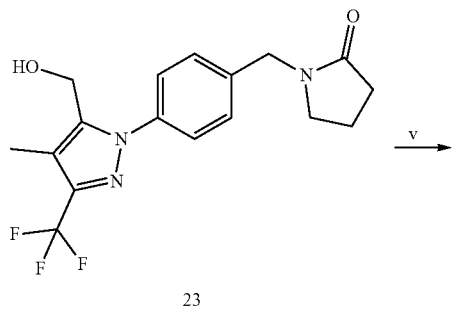
23

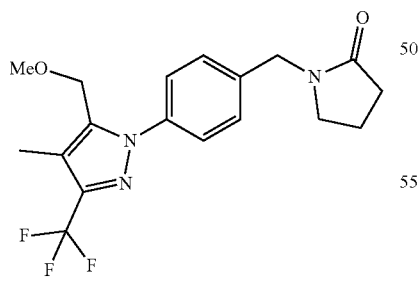
24

Scheme 3: Reagents and conditions: (i) 2,2,2-trifluoroethylamine hydrochloride, sodium nitrite, DCM:H₂O (2:1), 0° C. to RT, 1 week, 70%; (ii) bromine, Et₂O, 0° C. to RT, 20 h, 93%; (iii) LiAlH₄, THF, 0° C. to RT, 24 h, 88%; (iv) 1-[(4-iodophenyl)methyl]pyrrolidin-2-one (2), N,N-dimethylglycine, copper(I) oxide, caesium carbonate, DMSO, 130° C., 18 h, 48%; (v) NaH (60% dispersion in mineral oil), iodomethane, THF, 0° C. to RT, 72 h, 93%

30

Scheme 4

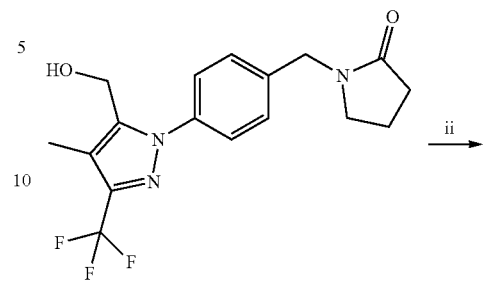
23

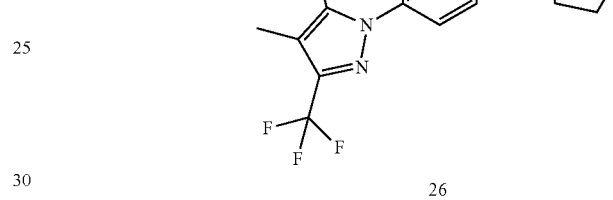
26

Scheme 4: Reagents and conditions: (ii) ammonium acetate, (diacetoxyiodo)benzene, TEMPO, MeCN:H₂O (9:1), RT, 18 h, 22%.

Scheme 5

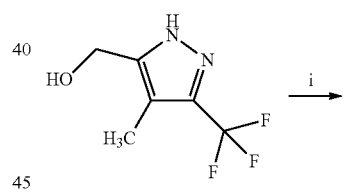

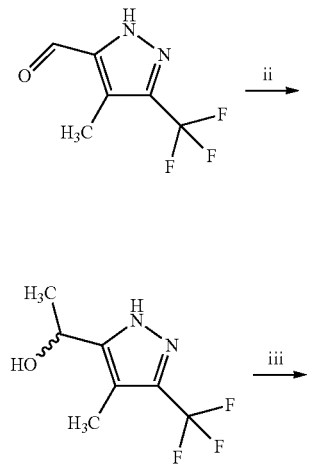

-continued

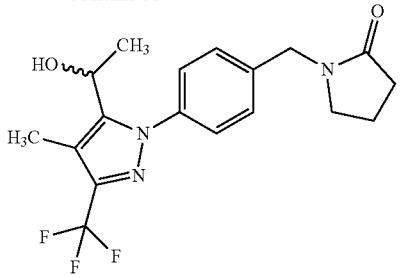

Scheme 5: Reagents and conditions: (i) MnO$_2$, THF, RT, 40 h, 99% (ii) MeMgBr (3M in Et$_2$O), THF, 0° C. to RT, 24 h, 73% (iii) 1-[(4-iodophenyl)methyl]pyrrolidin-2-one (2), N,N-dimethylglycine, copper(I) oxide, caesium carbonate, DMSO, 130° C., 18 h, 64%.

Certain of the intermediates disclosed herein are novel and form a further aspect of the invention. In certain embodiments the novel intermediate is a compound of the formula (IV):

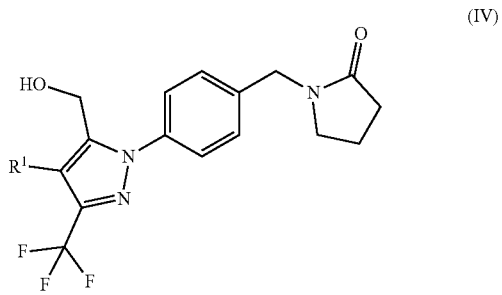

(IV)

wherein R$^1$ is as defined herein. Suitably is R$^1$ is C$_{1-4}$ alkyl. A particular compound of the formula (IV) is the compound of the formula (IVa):

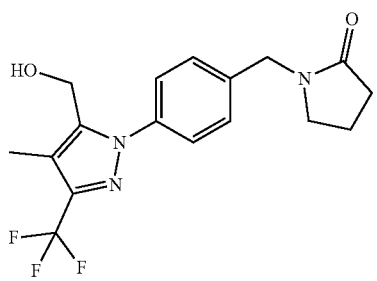

(IVa)

EXAMPLES

Throughout this specification these abbreviations have the following meanings:
Aq.=aqueous
DCM=dichloromethane
DMF=N,N-dimethylformamide
DMSO=dimethyl sulfoxide
Et=ethyl
EtOAc=ethyl acetate
h=hours
HBSS=Hank's Balanced Salt Solution
HEPES=4-(2-Hydroxyethyl)-1-piperazineethanesulponic acid
Me=methyl
min=minutes
mol=mole
$^c$Pr=cyclopropyl
$^i$Pr=isopropyl
R$_t$=retention time
RT=room temperature
Sat.=saturated
TEMPO=(2,2,6,6-Tetramethylpiperidin-1-yl)oxyl
THF=tetrahydrofuran
T3P=propylphosphonic anhydride Solvents, reagents and starting materials were purchased from commercial vendors and used as received unless otherwise described. All reactions were performed at room temperature unless otherwise stated.

LCMS data was recorded on a Waters 2695 HPLC using a Waters 2487 UV detector and a Thermo LCQ ESI-MS. Samples were eluted through a Phenomenex Luna 3μ C18 50 mm×4.6 mm column, using water and acetonitrile acidified by 0.1% formic acid at 1.5 mL/min and detected at 254 nm.

The gradient employed was:

| Time (minutes) | % Water + 0.1% formic acid | % MeCN + 0.1% formic acid |
| --- | --- | --- |
| 0.0 | 70 | 30 |
| 5.0 | 10 | 90 |
| 6.0 | 10 | 90 |
| 6.5 | 70 | 30 |
| 7.0 | 70 | 30 |

NMR was also used to characterise final compounds. NMR spectra were recorded at 500 MHz on a Varian VNMRS 500 MHz spectrometer (at 30° C.), using residual isotopic solvent (CHCl$_3$, δ$_H$=7.27 ppm, DMSO δ$_H$=2.50 ppm, MeOH H=3.31 ppm) as an internal reference. Chemical shifts are quoted in parts per million (ppm). Coupling constants (J) are recorded in Hertz.

General procedure A: To a suspension of magnesium chloride (1 mol equiv.) in DCM was added the appropriate ketoester (1 mol equiv.). After 15 min, the reaction mixture was cooled to 0° C. and pyridine (2 mol equiv.) slowly added over 5-10 min. After a further 30 min at 0° C., trifluoroacetic anhydride (1.1 mol equiv.) was added dropwise and the reaction temperature allowed to warm to room temperature. After 18 h the reaction was quenched by cautious addition of 2 M aq. HCl (10 mL). The aqueous layer was extracted with DCM (3×20 mL), the combined organic layers were washed with brine (30 mL), dried over MgSO$_4$ and concentrated in vacuo to afford a crude yellow liquid. The crude liquid was diluted in EtOH and hydrazine monohydrate (1 mol equiv.) added to the solution. The reaction mixture was stirred at 78° C. for 18 h. Upon completion, the reaction mixture was concentrated under reduced pressure. The crude product was purified by column chromatography.

General procedure B: To the appropriate pyrazole ester (1 mol equiv.) in THF, cooled to 0° C., was added lithium aluminium hydride pellets (1.5 mol equiv.). The reaction was stirred at 0° C. for 30 min, then allowed to warm to room temperature and stirred at this temperature overnight. Upon completion, the reaction mixture was quenched by cautious addition of saturated aq. Rochelle salt (15 mL) and stirred at room temperature for an extra hour. The layers were separated, the aqueous layer was extracted with EtOAc (3×20 mL), the combined organic layers were washed with brine (30 mL), dried over MgSO$_4$ and concentrated under reduced pressure. The crude product was purified by column chromatography.

General procedure C: To 1-[(4-iodophenyl)methyl]pyrrolidin-2-one (2) (1 mol equiv.), N,N-dimethylglycine (1 mol equiv.), caesium carbonate (2 mol equiv.) and copper(I) oxide (0.2 mol equiv.) in DMSO was added the appropriate pyrazole. The resulting reaction mixture was degassed with nitrogen for 5 minutes and then heated at 130° C. for 18 h. Upon completion, the reaction mixture was diluted with EtOAc (15 mL), washed with brine (2×15 mL), dried over MgSO$_4$ and concentrated in vacuo. The crude product was purified by column chromatography.

1-[(4-Iodophenyl)methyl]pyrrolidin-2-one, (2)

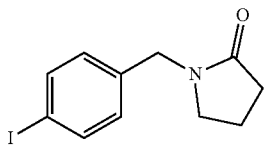 [SMILES: O=C1CCCN1Cc1ccc(I)cc1]

The title compound was synthesised according to a literature procedure (Ward et al. Integration of Lead Optimization with Crystallography for a Membrane-Bound Ion Channel Target: Discovery of a New Class of AMPA Receptor Positive Allosteric Modulators. J. Med. Chem. 2011, 54 (1), 78-94) and illustrated in Scheme 1 above; $R_f$=0.29 (petrol: EtOAc—1:1); $^1$H NMR (500 MHz, DMSO-d$_6$) δ 1.91 (p, J=7.5 Hz, 2H), 2.27 (t, J=8.0 Hz, 2H), 3.21 (t, J=7.0 Hz, 2H), 4.31 (s, 2H), 7.03 (d, J=7.9 Hz, 2H), 7.69 (d, J=8.0 Hz, 2H). LCMS product at $R_t$=0.77 min and ES$^+$ m/z 301.99 [M+H]$^+$.

Ethyl 5-methyl-3-(trifluoromethyl)-1H-pyrazole-4-carboxylate, (7)

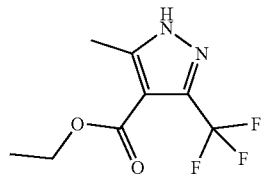

Compound 7 was synthesised according to general procedure A, using the following reagents: magnesium chloride (732 mg, 7.7 mmol), ethyl acetoacetate (3) (0.97 mL, 7.7 mmol), pyridine (1.24 mL, 15.4 mmol), trifluoroacetic anhydride (1.17 mL, 8.4 mmol), DCM (10 mL), hydrazine monohydrate (0.41 mL, 8.45 mmol) and EtOH (15 mL). The crude product was purified by column chromatography on silica gel (petrol:EtOAc—1:0 to 8:2) to afford the title compound as a white solid (377 mg, 22%); $R_f$=0.34 (petrol: EtOAc—8:2); $^1$H NMR (500 MHz, chloroform-d) δ 1.37 (t, J=7.1 Hz, 3H), 2.59 (s, 3H), 4.34 (q, J=7.1 Hz, 2H); LCMS product at $R_t$=2.70 min and ES$^+$ m/z 223.07 [M+H]$^+$ Ethyl 5-ethyl-3-(trifluoromethyl)-1H-pyrazole-4-carboxylate, (8)

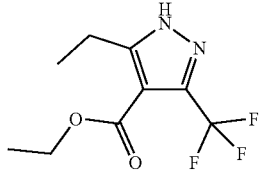 [SMILES: CCOC(=O)c1c(C(F)(F)F)n[nH]c1CC]

Compound 8 was synthesised according to general procedure A, using the following reagents: magnesium chloride (647 mg, 6.8 mmol), ethyl 3-oxopentanoate (4) (1.0 mL, 6.8 mmol), pyridine (1.1 mL, 13.6 mmol), trifluoroacetic anhydride (1.04 mL, 7.5 mmol), DCM (15 mL), hydrazine monohydrate (0.36 mL, 7.5 mmol) and EtOH (15 mL). The crude product was purified by column chromatography on silica gel (petrol:EtOAc—1:0 to 85:15) to afford the title compound as a white solid (243 mg, 15%); $R_f$=0.28 (petrol: EtOAc—85:15); $^1$H NMR (500 MHz, DMSO-d$_6$) δ 1.21 (t, J=7.5 Hz, 3H), 1.26 (t, J=7.1 Hz, 3H), 2.91 (q, J=7.6 Hz, 2H), 4.23 (q, J=7.1 Hz, 2H); LCMS product at $R_t$=0.59 min and ES$^+$ m/z 237.09 [M+H]$^+$ Ethyl 5-isopropyl-3-(trifluoromethyl)-1H-pyrazole-4-carboxylate, (9)

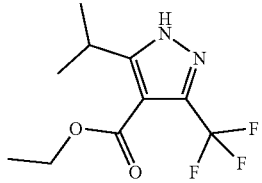 [SMILES: CCOC(=O)c1c(C(F)(F)F)n[nH]c1C(C)C]

Compound 9 was synthesised according to general procedure A, using the following reagents: magnesium chloride (590 mg, 6.2 mmol), ethyl 4-methyl-3-oxopentanoate (5) (1.0 mL, 6.2 mmol), pyridine (1.0 mL, 12.4 mmol), trifluoroacetic anhydride (0.95 mL, 6.8 mmol), DCM (15 mL), hydrazine monohydrate (0.33 mL, 6.8 mmol) and EtOH (15 mL). The crude product was purified by column chromatography on silica gel (petrol:EtOAc—1:0 to 85:15) to afford the title compound as a white solid (652 mg, 42%); $R_f$=0.31 (petrol:EtOAc—85:15); $^1$H NMR (500 MHz, DMSO-d$_6$) δ 1.22-1.32 (m, 9H), 3.63 (hept, J=6.9 Hz, 1H), 4.24 (q, J=7.1 Hz, 2H), 13.79 (s, 1H); LCMS product at $R_t$=2.28 min and ES$^+$ m/z 251.30 [M+H]$^+$ Ethyl 5-cyclopropyl-3-(trifluoromethyl)-1H-pyrazole-4-carboxylate, (10)

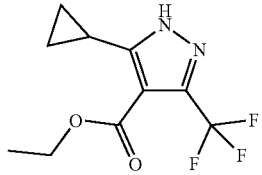 [SMILES: CCOC(=O)c1c(C(F)(F)F)n[nH]c1C1CC1]

Compound 10 was synthesised according to general procedure A, using the following reagents: magnesium chloride (1.29 g, 13.5 mmol), ethyl 3-cyclopropyl-3-oxo-propanoate (6) (2.0 mL, 13.5 mmol), pyridine (2.19 mL, 27.1 mmol), trifluoroacetic anhydride (2.07 mL, 14.9 mmol), DCM (15 mL), hydrazine monohydrate (0.72 mL, 14.9 mmol) and EtOH (15 mL). The crude product was purified by column chromatography on silica gel (petrol:EtOAc—1:0 to 8:2) to afford the title compound as a white solid (95 mg, 3%); $R_f$=0.35 (petrol:EtOAc—8:2); $^1$H NMR (500 MHz, chloroform-d) δ 0.86 (q, J=5.5 Hz, 2H), 1.16 (q, J=6.3 Hz, 2H), 1.37 (t, J=7.1 Hz, 3H), 2.56 (ddd, J=14.0, 8.6, 5.4 Hz, 1H), 4.35 (q, J=7.1 Hz, 2H). LCMS product at $R_t$=3.31 min and ES$^+$ m/z 249.06 [M+H]$^+$

[5-Methyl-3-(trifluoromethyl)-1H-pyrazol-4-yl]methanol, (11)

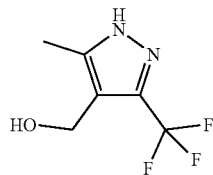

Compound 11 was synthesised according to general procedure B, using the following reagents: ethyl 5-methyl-3-(trifluoromethyl)-1H-pyrazole-4-carboxylate (7) (580 mg, 2.61 mmol), lithium aluminium hydride (149 mg, 3.92 mmol) and THF (8 mL). The crude product was purified by column chromatography on silica gel (petrol:EtOAc—1:0 to 1:1) to afford the title compound as a white solid (465 mg, 99%); $R_f$=0.29 (petrol:EtOAc—1:1; KMnO$_4$); $^1$H NMR (500 MHz, DMSO-d$_6$) δ 2.26 (s, 3H), 4.35 (d, J=5.1 Hz, 2H), 4.79 (t, J=5.1 Hz, 1H), 13.14 (s, 1H); LCMS product at $R_t$=0.70 min and ES$^+$ m/z 181.12 [M+H]$^+$

[5-Ethyl-3-(trifluoromethyl)-1H-pyrazol-4-yl]methanol, (12)

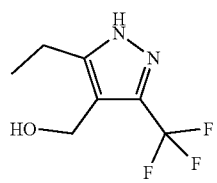

Compound 12 was synthesised according to general procedure B, using the following reagents: ethyl 5-ethyl-3-(trifluoromethyl)-1H-pyrazole-4-carboxylate (8) (700 mg, 2.96 mmol), lithium aluminium hydride pellets (169 mg, 4.45 mmol) and THF (15 mL). The crude product was purified by column chromatography on silica gel (petrol:EtOAc—1:0 to 1:1) to afford the title compound as a white solid (548 mg, 95%); $R_f$=0.35 (petrol:EtOAc—1:1; phosphomolybdic acid); $^1$H NMR (500 MHz, DMSO-d$_6$) δ 1.19 (t, J=7.6 Hz, 3H), 2.67 (q, J=7.6 Hz, 2H), 4.36 (d, J=5.1 Hz, 2H), 4.81 (t, J=5.1 Hz, 1H), 13.18 (s, 1H); LCMS product at $R_t$=0.60 min and ES$^+$ m/z 195.12 [M+H]$^+$

[5-Isopropyl-3-(trifluoromethyl)-1H-pyrazol-4-yl]methanol, (13)

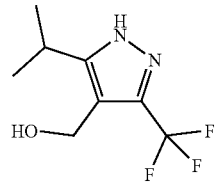

Compound 13 was synthesised according to general procedure B, using the following reagents: ethyl 5-isopropyl-3-(trifluoromethyl)-1H-pyrazole-4-carboxylate (9) (1.3 g, 5.2 mmol), lithium aluminium hydride pellets (0.30 g, 7.79 mmol) and THF (20 mL). The crude product was purified by column chromatography on silica gel (petrol:EtOAc—1:0 to 1:1) to afford the title compound as a white solid (1.02 g, 94%); $R_f$=0.38 (petrol:EtOAc—1:1; phosphomolybdic acid); $^1$H NMR (500 MHz, DMSO-d$_6$) δ 1.25 (d, J=7.1 Hz, 6H), 3.17 (hept, J=7.0 Hz, 1H), 4.37 (d, J=5.0 Hz, 2H), 4.80 (t, J=5.0 Hz, 1H), 13.17 (s, 1H); LCMS product at $R_t$=0.88 min and ES$^+$ m/z 209.36 [M+H]$^+$

[5-Cyclopropyl-3-(trifluoromethyl)-1H-pyrazol-4-yl]methanol, (14)

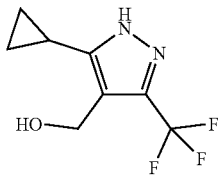 [SMILES: OCc1c(C(F)(F)F)n[nH]c1C1CC1]

Compound 14 was synthesised according to general procedure B, using the following reagents: ethyl 5-cyclopropyl-3-(trifluoromethyl)-1H-pyrazole-4-carboxylate (10) (90 mg, 0.36 mmol), lithium aluminium hydride pellets (21 mg, 0.54 mmol) and THF (2 mL). The crude product was purified by column chromatography on silica gel (petrol:EtOAc—1:0 to 6:4) to afford the title product as a white solid (55 mg, 73%); $R_f$=0.28 (petrol:EtOAc—6:4; KMnO$_4$); $^1$H NMR (500 MHz, DMSO-d$_6$) δ 0.80-0.85 (m, 2H), 0.92-0.98 (m, 2H), 1.98 (tt, J=8.6, 5.3 Hz, 1H), 4.42 (d, J=5.0 Hz, 2H), 4.83 (t, J=4.9 Hz, 1H), 12.97 (s, 1H); LCMS product at $R_t$=0.85 min and ES$^+$ m/z 207.06 [M+H]$^+$ Methyl 4-methyl-5-(trifluoromethyl)-4,5-dihydro-1H-pyrazole-3-carboxylate, (20)

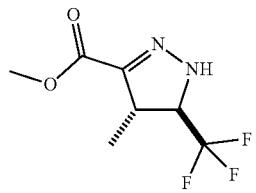

To methyl crotonate (19) (1.0 mL, 9.43 mmol) in DCM (10 mL) was added a solution of sodium nitrite (0.98 g, 14.1 mmol) in water (5 mL) at room temperature. The resulting heterogeneous solution was cooled to 0° C. and 2,2,2-trifluoroethylamine hydrochloride (1.92 g, 14.1 mmol) was added in small portions. Once the addition was complete, the reaction mixture was vigorously stirred at 0° C. for 1 h and then allowed to warm to room temperature. After one week, the reaction was diluted with water (10 mL), the aqueous layer was extracted with DCM (3×20 mL), the combined organic layers were washed with brine (30 mL), dried over MgSO$_4$ and concentrated in vacuo to afford a crude oil. The crude product was purified by column chromatography on silica gel (petrol:EtOAc—1:0 to 8:2) to yield the title compound as a clear oil (1.41 g, 70%); R$_f$=0.31 (petrol:EtOAc—8:2); $^1$H NMR (500 MHz, chloroform-d) δ 1.40 (d, J=7.1 Hz, 3H), 3.51 (p, J=7.0 Hz, 1H), 3.85 (s, 3H), 3.95 (p, J=7.1 Hz, 1H), 6.38 (s, 1H); LCMS product at R$_t$=1.60 min, m/z of the desired product was not detected Methyl 4-methyl-3-(trifluoromethyl)-1H-pyrazole-5-carboxylate, (21)

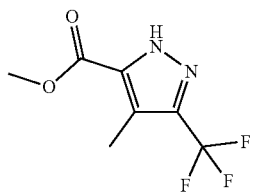

To methyl 4-methyl-5-(trifluoromethyl)-4,5-dihydro-1H-pyrazole-3-carboxylate (20) (8.2 g, 39.0 mmol) in diethyl ether (100 mL), cooled to 0° C., was added bromine (2.4 mL, 46.8 mmol) dropwise. The resulting mixture was allowed to warm to room temperature and stirred at this temperature for 20 h. Upon completion, the reaction mixture was concentrated in vacuo and the orange residue dissolved in EtOAc (40 mL). The organic layer was washed with sat. aq. Na$_2$S$_2$O$_3$ (30 mL), sat. aq. NaHCO$_3$ (30 mL) and brine (30 mL), dried over MgSO$_4$ and concentrated under reduced pressure to afford a yellow oil. The crude yellow oil was purified by column chromatography on silica gel (petrol:EtOAc—1:0 to 85:15) to yield the title compound as an off-white solid (7.65 g, 93%); R$_f$=0.26 (petrol:EtOAc—85:15); $^1$H NMR (500 MHz, DMSO-d$_6$) δ 2.31 (s, 3H), 3.87 (s, 3H); LCMS product at R$_t$=0.48 min and ES$^+$ m/z 208.93 [M+H]$^+$

[4-Methyl-3-(trifluoromethyl)-1H-pyrazol-5-yl]methanol, (22)

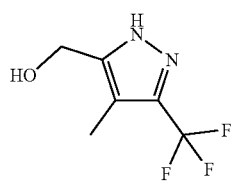

Compound 22 was synthesised according to general procedure B, using the following reagents: methyl 4-methyl-3-(trifluoromethyl)-1H-pyrazole-5-carboxylate (21) (400 mg, 1.92 mmol), lithium aluminium hydride pellets (109 mg, 2.88 mmol) and THF (5 mL). The crude product was purified by column chromatography on silica gel (petrol:EtOAc—1:0 to 1:1) to afford the title compound as a white solid (305 mg, 88%); R$_f$=0.34 (petrol:EtOAc—1:1); $^1$H NMR (500 MHz, DMSO-d$_6$) δ 2.05 (s, 3H), 4.46 (d, J=4.0 Hz, 2H), 5.29 (s, 1H), 13.28 (s, 1H); LCMS product at R$_t$=1.20 min and ES$^+$ m/z 180.91 [M+H]$^+$ 4-Methyl-3-(trifluoromethyl)-1H-pyrazole-5-carbaldehyde, (27)

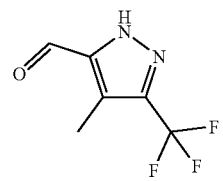

To [4-methyl-3-(trifluoromethyl)-1H-pyrazol-5-yl]methanol (22) (800 mg, 4.44 mmol) in THF (80 mL) was added manganese(IV) oxide (5.79 g, 66.6 mmol) at room temperature. The resulting heterogeneous reaction mixture was stirred at this temperature for 40 h. Upon completion, the reaction mixture was filtered through a pad of Celite and concentrated in vacuo to give a yellow oil. The crude product was purified by column chromatography on silica gel (petrol:EtOAc—1:0 to 8:2) to yield the title compound as a white solid (755 mg, 95%); R$_f$=0.33 (petrol:EtOAc—85:15); $^1$H NMR (500 MHz, DMSO-d$_6$) δ 2.38 (s, 3H), 9.94 (s, 1H); LCMS product at R$_t$=1.17 min and m/z of the desired product was not detected 1-[4-Methyl-3-(trifluoromethyl)-1H-pyrazol-5-yl]ethanol, (29)

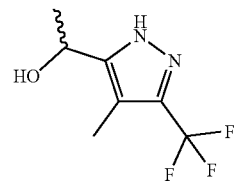

To 4-methyl-3-(trifluoromethyl)-1H-pyrazole-5-carbaldehyde (27) (750 mg, 4.21 mmol) in THF (14 mL), cooled to 0° C. was added methylmagnesium bromide solution (3 M in diethyl ether) (5.61 mL, 16.8 mmol) dropwise. After 15 min, the solution was allowed to warm to room temperature and stirred for a further 72 h (for convenience). Upon completion, the reaction mixture was quenched by addition of sat. aq. ammonium chloride (15 mL). The layers were separated, the aqueous layer was extracted with EtOAc (3×20 mL), the combined organic layers were washed with brine (30 mL), dried over MgSO$_4$ and concentrated under reduced pressure to afford a crude white solid. The crude product was purified by column chromatography on silica gel (petrol:EtOAc—1:0 to 6:4) to afford the title compound as a white solid (600 mg, 73%); R$_f$=0.32 (petrol:EtOAc—6:4; KMnO$_4$); $^1$H NMR (500 MHz, DMSO-d$_6$) δ 1.38 (d, J=6.6 Hz, 3H), 2.06 (s, 3H), 4.85 (qd, J=6.6, 4.0 Hz, 1H), 5.42 (d, J=3.9 Hz, 1H), 13.19 (s, 1H).

Example 1: 1-[[4-[4-(Hydroxymethyl)-5-methyl-3-(trifluoromethyl)pyrazol-1-yl]phenyl]methyl]pyrrolidin-2-one, (15)

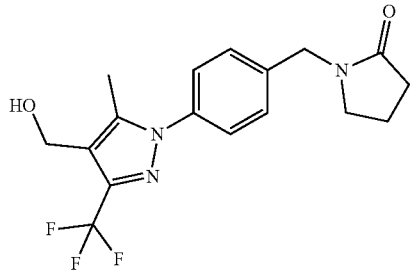 [SMILES: Cc1c(CO)c(C(F)(F)F)nn1-c1ccc(CN2CCCC2=O)cc1]

Compound 15 was synthesised according to general procedure C, using the following reagents: [5-methyl-3-(trifluoromethyl)-1H-pyrazol-4-yl]methanol (11) (48 mg, 0.27 mmol), 1-[(4-iodophenyl)methyl]pyrrolidin-2-one (2) (80 mg, 0.27 mmol), N,N-dimethylglycine (25 mg, 0.24 mmol), caesium carbonate (157 mg, 0.48 mmol), copper(I) oxide (7 mg, 0.05 mmol) and DMSO (0.5 mL). The crude product was purified by column chromatography on silica gel (EtOAc:MeOH—1:0 to 97:3) to afford the title product as a white solid (72 mg, 77%); $R_f$=0.33 (EtOAc—100%); $^1$H NMR (500 MHz, DMSO-$d_6$) δ 1.92-1.98 (m, 2H), 2.28-2.34 (m, 5H), 3.29 (t, J=7.2 Hz, 2H), 4.44 (d, J=5.3 Hz, 2H), 4.46 (s, 2H), 5.01 (t, J=5.1 Hz, 1H), 7.40 (d, J=8.1 Hz, 2H), 7.51 (d, J=8.2 Hz, 2H); LCMS product at $R_t$=1.41 min and ES$^+$ m/z 354.08 [M+H]$^+$ Example 2: 1-[[4-[5-Ethyl-4-(hydroxymethyl)-3-(trifluoromethyl)pyrazol-1-yl]phenyl]methyl]pyrrolidin-2-one, (16)

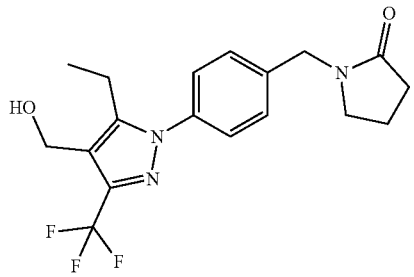 [SMILES: CCc1c(CO)c(C(F)(F)F)nn1-c1ccc(CN2CCCC2=O)cc1]

Compound 16 was synthesised according to general procedure C, using the following reagents: 1-[(4-iodophenyl)methyl]pyrrolidin-2-one (80 mg, 0.27 mmol) (2), [5-ethyl-3-(trifluoromethyl)-1H-pyrazol-4-yl]methanol (12) (52 mg, 0.27 mmol), copper(I)oxide (8 mg, 0.05 mmol), N,N-dimethylglycine (27 mg, 0.27 mmol), caesium carbonate (173 mg, 0.53 mmol) and DMSO (0.5 mL). The crude product was purified by column chromatography on silica gel (petrol:EtOAc—1:1 to 0:1) to afford the title compound as white solid (68 mg, 70%); $R_f$=0.31 (EtOAc—100%); $^1$H NMR (500 MHz, DMSO-$d_6$) δ 7.47 (d, J=8.3 Hz, 2H), 7.41 (d, J=8.3 Hz, 2H), 5.03 (t, J=5.0 Hz, 1H), 4.50-4.42 (m, 4H), 3.29-3.26 (m, 2H), 2.70 (q, J=7.6 Hz, 2H), 2.31 (t, J=8.1 Hz, 2H), 2.01-1.91 (m, 2H), 1.00 (t, J=7.5 Hz, 3H); LCMS product at $R_t$=0.47 min and ES$^+$ m/z 368.09 [M+H]$^+$ Example 3: 1-[[4-[4-(Hydroxymethyl)-5-isopropyl-3-(trifluoromethyl)pyrazol-1-yl]phenyl]methyl]pyrrolidin-2-one, (17)

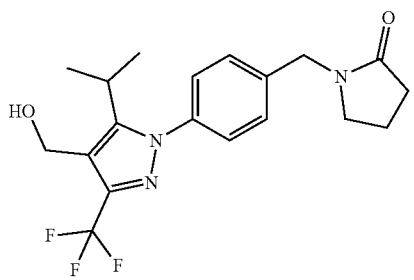 [SMILES: CC(C)c1c(CO)c(C(F)(F)F)nn1-c1ccc(CN2CCCC2=O)cc1]

Compound 17 was synthesised according to general procedure C, using the following reagents: 1-[(4-iodophenyl)methyl]pyrrolidin-2-one (2) (80 mg, 0.27 mmol), [5-isopropyl-3-(trifluoromethyl)-1H-pyrazol-4-yl]methanol (13) (55 mg, 0.27 mmol), copper(I)oxide (8 mg, 0.05 mmol), N,N-dimethylglycine (27 mg, 0.27 mmol), caesium carbonate (173 mg, 0.53 mmol) and DMSO (0.5 mL). The crude product was purified by column chromatography on silica gel (petrol:EtOAc—1:1 to 0:1) to afford the title compound as clear oil (67 mg, 66%); $R_f$=0.35 (EtOAc—100%); $^1$H NMR (500 MHz, DMSO-$d_6$) δ 1.24 (d, J=7.1 Hz, 6H), 1.92-2.01 (m, 2H), 2.31 (t, J=8.0 Hz, 2H), 2.99 (dt, J=14.3, 7.1 Hz, 1H), 3.27-3.30 (m, 2H), 4.47 (s, 2H), 4.52 (d, J=4.5 Hz, 2H), 5.03 (t, J=4.6 Hz, 1H), 7.38-7.45 (m, 4H); LCMS product at $R_t$=0.49 min and ES$^+$ m/z 382.14 [M+H]$^+$ Example 4: 1-[[4-[5-Cyclopropyl-4-(hydroxymethyl)-3-(trifluoromethyl)pyrazol-1-yl]phenyl]methyl]pyrrolidin-2-one, (18)

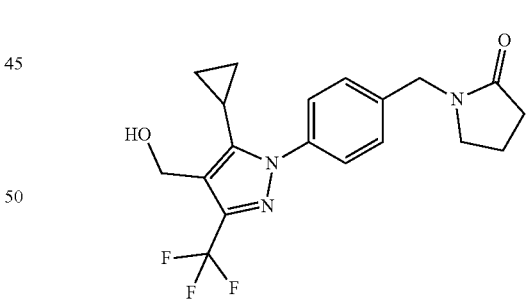

Compound 18 was synthesised according to general procedure C, using the following reagents: [5-cyclopropyl-3-(trifluoromethyl)-1H-pyrazol-4-yl]methanol (14) (55 mg, 0.27 mmol), 1-[(4-iodophenyl)methyl]pyrrolidin-2-one (2) (80.mg, 0.27 mmol), N,N-dimethylglycine (25 mg, 0.24 mmol), caesium carbonate (157 mg, 0.48 mmol), copper(I) oxide (7 mg, 0.05 mmol) and DMSO (0.5 mL). The crude product was purified by column chromatography on silica gel (petrol:EtOAc—1:1 to 0:1) to afford the title compound as a clear oil (63 mg, 63%); $R_f$=0.33 (EtOAc—100%)$^1$H NMR (500 MHz, DMSO-$d_6$) δ 0.55-0.60 (m, 2H), 0.79-0.84 (m, 2H), 1.91-1.99 (m, 3H), 2.32 (t, J=8.1 Hz, 2H), 3.28 (t, J=7.1 Hz, 2H), 4.46 (s, 2H), 4.49 (d, J=4.9 Hz, 2H), 4.96 (t, J=4.8 Hz, 1H), 7.38 (d, J=8.4 Hz, 2H), 7.58 (d, J=8.4 Hz, 2H); LCMS product at $R_t$=2.67 min and ES$^+$ m/z 380.11 [M+H]$^+$ Example 5: 1-[[4-[5-(Methoxymethyl)-4-methyl-3-(trifluoromethyl)pyrazol-1-yl]phenyl]methyl]pyrrolidin-2-one, (24)

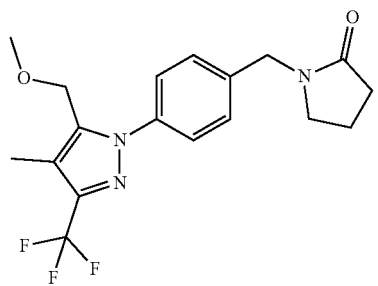 [SMILES: COCc1c(C)c(C(F)(F)F)nn1-c1ccc(CN2CCCC2=O)cc1]

To 1-[[4-[5-(hydroxymethyl)-4-methyl-3-(trifluoromethyl)pyrazol-1-yl]phenyl]methyl]pyrrolidin-2-one (23) (70 mg, 0.20 mmol) in THF (1 mL) was added sodium hydride (60% dispersion in mineral oil) (12 mg, 0.30 mmol) at room temperature. After 15 min, iodomethane (62 μL, 0.99 mmol) was added dropwise and the resulting reaction mixture stirred at room temperature for 72 h (for convenience). Upon completion, the reaction mixture was quenched by addition of brine (15 mL). The layers were separated, the aqueous layer was extracted with EtOAc (3×20 mL), the combined organic layers were washed with brine (30 mL), dried over MgSO$_4$ and concentrated under reduced pressure to afford a crude yellow solid. The crude product was purified by column chromatography on silica gel (petrol:EtOAc—1:1 to 5:95) to afford the title compound as an off-white solid (68 mg, 93%); $R_f$=0.29 (petrol:EtOAc—5:95); $^1$H NMR (500 MHz, DMSO-d$_6$) δ 1.91-2.01 (m, 2H), 2.20 (s, 3H), 2.32 (t, J=8.0 Hz, 2H), 3.25 (s, 3H), 3.29 (t, J=7.0 Hz, 2H), 4.37 (s, 2H), 4.45 (s, 2H), 7.40 (d, J=8.2 Hz, 2H), 7.55 (d, J=8.2 Hz, 2H); LCMS product at $R_t$=3.66 min and ES$^+$ m/z 367.91 [M+H]$^+$ The starting material, 1-[[4-[5-(hydroxymethyl)-4-methyl-3-(trifluoromethyl)pyrazol-1-yl]phenyl]methyl]pyrrolidin-2-one, (23)

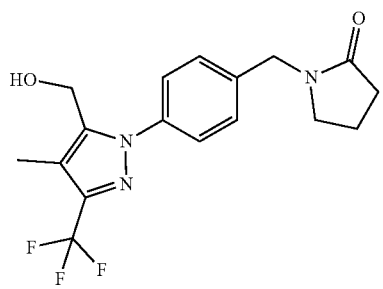 [SMILES: Cc1c(C(F)(F)F)nn(-c2ccc(CN3CCCC3=O)cc2)c1CO]

was prepared according to general procedure C, using the following reagents: [4-methyl-3-(trifluoromethyl)-1H-pyrazol-5-yl]methanol (22) (48 mg, 0.27 mmol), 1-[(4-iodophenyl)methyl]pyrrolidin-2-one (2) (80 mg, 0.27 mmol), N,N-dimethylglycine (25 mg, 0.24 mmol), caesium carbonate (157 mg, 0.48 mmol), copper(I)oxide (7 mg, 0.05 mmol) and DMSO (0.5 mL). The crude product was purified by column chromatography on silica gel (EtOAc:MeOH—1:0 to 97:3) to afford the title compound (23) as a white solid (45 mg, 48%); $R_f$=0.27 (EtOAc—100%); $^1$H NMR (500 MHz, DMSO-d$_6$) δ 1.91-1.98 (m, 2H), 2.19 (s, 3H), 2.31 (t, J=8.1 Hz, 2H), 3.27-3.29 (m, 4H), 4.42 (d, J=5.3 Hz, 2H), 4.45 (s, 2H), 5.49 (t, J=5.3 Hz, 1H), 7.40 (d, J=8.3 Hz, 2H), 7.62 (d, J=8.4 Hz, 2H); LCMS product at $R_t$=2.58 min and ES$^+$ m/z 353.91 [M+H]$^+$ Example 6: 4-Methyl-2-[4-[(2-oxopyrrolidin-1-yl)methyl]phenyl]-5-(trifluoromethyl)pyrazole-3-carbonitrile, (26)

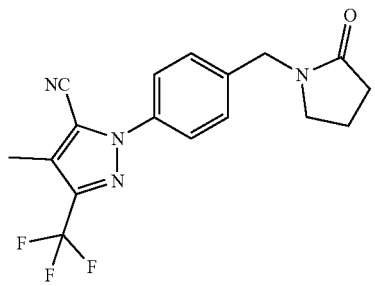 [SMILES: Cc1c(C(F)(F)F)nn(-c2ccc(CN3CCCC3=O)cc2)c1C#N]

To 1-[[4-[5-(hydroxymethyl)-4-methyl-3-(trifluoromethyl)pyrazol-1-yl]phenyl]methyl]pyrrolidin-2-one (23) (110 mg, 0.31 mmol) in acetonitrile (1.8 mL) and water (0.2 mL) was added (diacetoxyiodo)benzene (221 mg, 0.68 mmol), TEMPO (2 mg, 0.02 mmol) and ammonium acetate (96 mg, 1.25 mmol). The reaction mixture was stirred at room temperature for 18 h before being concentrated under reduced pressure. The reaction mixture was diluted with water (10 mL) and extracted with ethyl acetate (3×10 mL). The combined organic extracts were dried over MgSO$_4$, filtered and concentrated under reduced pressure. The residue was purified by column chromatography on silica gel (petrol:EtOAc—1:0 to 0:1). The desired fractions were concentrated under reduced pressure to give the title compound as a pale yellow oil (25 mg, 22%); $R_f$=0.48 (petrol:EtOAc—1:4); $^1$H NMR (500 MHz, chloroform-d) δ 7.67 (d, J=8.5 Hz, 2H), 7.43 (d, J=8.5 Hz, 2H), 4.53 (s, 2H), 3.30 (t, J=7.1 Hz, 2H), 2.47 (t, J=8.1 Hz, 2H), 2.41 (s, 3H), 2.10-1.98 (m, 2H); LCMS product at $R_t$=2.95 min and ES$^+$ m/z 349.04 (M+H)+

Example 7: 1-[[4-[5-(1-Hydroxyethyl)-4-methyl-3-(trifluoromethyl)pyrazol-1-yl]phenyl]methyl]pyrrolidin-2-one, (31)

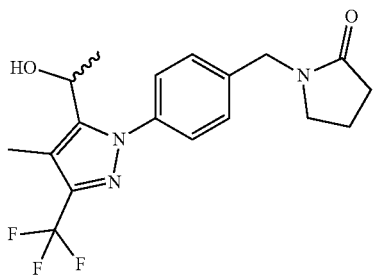 [SMILES: Cc1c(C(F)(F)F)nn(-c2ccc(CN3CCCC3=O)cc2)c1C(C)O]

Compound 31 was synthesised according to general procedure C, using the following reagents: 1-[(4-iodophenyl)methyl]pyrrolidin-2-one (2) (80 mg, 0.27 mmol), 1-[4-methyl-3-(trifluoromethyl)-1H-pyrazol-5-yl]ethanol (29) (52 mg, 0.27 mmol), copper(I)oxide (8 mg, 0.05 mmol), N,N-dimethylglycine (27 mg, 0.27 mmol), caesium carbonate (173 mg, 0.53 mmol) and DMSO (0.5 mL). The crude product was purified by column chromatography on silica gel (petrol:EtOAc—1:1 to 0:1) to afford the title compound as white solid (63 mg, 64%); $R_f$=0.28 (EtOAc—100%); $^1$H NMR (500 MHz, DMSO-$d_6$) δ 1.36 (d, J=6.7 Hz, 3H), 1.96 (dt, J=15.2, 6.5 Hz, 2H), 2.26 (s, 3H), 2.32 (t, J=8.0 Hz, 2H), 3.29 (t, J=7.0 Hz, 2H), 4.46 (s, 2H), 4.74 (dt, J=10.0, 5.0 Hz, 1H), 5.51 (d, J=3.3 Hz, 1H), 7.39 (d, J=8.2 Hz, 2H), 7.47 (d, J=8.2 Hz, 2H). LCMS product at $R_t$=3.17 min and ES$^+$ m/z 350.06 [M−H$_2$O]$^+$ Biological Data AMPA Calcium Ion Influx Assay The ability of the compounds of the invention to potentiate glutamate receptor-mediated response were determined using fluorescent calcium-indicator dye.

96 well plates were prepared containing confluent monolayer of HEK 293 cells stably expressing human GluR2 flip (unedited) AMPA receptor subunit (obtained from GlaxoSmithKline). These cells form functional homotetrameric AMPA receptors. The tissue culture medium in the wells was discarded and the wells were each washed three time with standard buffer for the cell line (145 μM NaCl, 5 mM KCl, 1 mM MgCl$_2$, 2 mM CaCl$_2$, 20 mM N-[2-hydroxyethyl]-piperazine-N-[2-ethanesulfonic acid (HEPES), 5.5 mM glucose, pH7.3). The plates were then incubated for 60 minutes in the dark with 2 μM Calcium 6 dye (Molecular Devices). After incubation each well was washed three times with buffer (80 μl).

Compounds of the invention were dissolved in dimethylsulfoxide (DMSO) at a stock concentration of 10 mM. These solutions were further diluted with DMSO. Each dilution (4 μl) to another compound plate and buffer (200 μl) was added. An agonist stimulus plate (glutamate) was prepared by dissolving sodium glutamate in water to give a concentration of 100 mM. This solution was diluted with buffer to give a final concentration of 500 μM and dispensed into another 96 well plate (200 μl/well).

The cell plate was then transferred to a fluorescence imaging plate reader such as the Flexstation 3 (Molecular Devices). A baseline fluorescence was taken over a 10 to 240 second period and then 40 μl from each plate containing a compound of the invention made up in standard buffer solution was added. Volumes were chosen to give a final concentration range of 40 μM to 4 pM. The fluorescence was then read over a 4 minute period. The activities of the compounds were determined by measuring peak fluorescence after the last addition. The activity can also be expressed relative to the fluorescence increase induced by cyclothiazide at their maximum response (i.e. greater than 40 uM).

Intrinsic Clearance (CLi)

The in-vitro intrinsic clearance of the compounds was measured in rat and human hepatocytes using the following assay.

5 μL microsomes (20 mg/ml, Corning BV) diluted into 95 μL PBS (pH 7) containing 0.2% DMSO and 4 μM test article were incubated at 37° C. shaking at 1000 rpm prior the addition of 100 μL of pre-warmed 4 mM NADPH in PBS (final concentrations: 0.5 mg/mL microsomes, 2 μM test article, 0.1% DMSO and 2 mM NADPH). After mixing thoroughly the T=0 sample (40 μL) was immediately quenched into ice cold methanol containing 2 μM internal standard (Carbemazapine). Three further samples were quenched in the same way at 3, 9 and 30 min. Samples were incubated on ice for 30 min before centrifugation at 4000 rpm+ for 200 min. The supernatant was analysed via LCMS and the test article:carbemazapine peak area ratios calculated to determine the rate of substrate depletion.

Biological Data

| Example (Compound #) | Structure | Mean % response at 40 μM | CLi (μl/min/mg) Rat, human |
|---|---|---|---|
| Example 1 (15) | 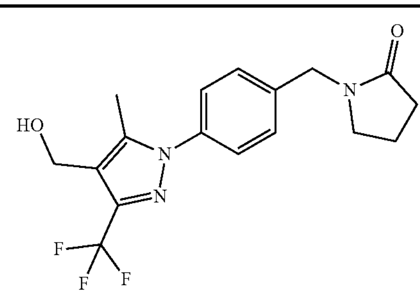 | 50 | 8.4, 4.3 |
| Example 2 (16) | 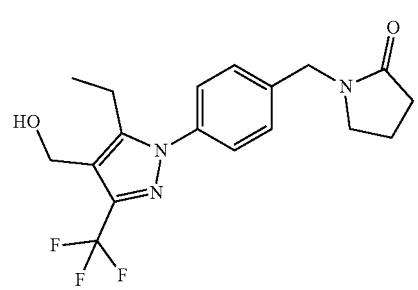 [SMILES: CCc1c(CO)c(C(F)(F)F)nn1-c1ccc(CN2CCCC2=O)cc1] | 75 | 3.7, 2.6 |

-continued

| Example (Compound #) | Structure | Mean % response at 40 μM | CLi (μl/min/mg) Rat, human |
|---|---|---|---|
| Example 3 (17) | (pyrazole with isopropyl, CH2OH, CF3, phenyl-CH2-pyrrolidinone) | 75 | 2.2, 7.9 |
| Example 4 (18) | (pyrazole with cyclopropyl, CH2OH, CF3, phenyl-CH2-pyrrolidinone) | 93 | NT |
| Example 5 (24) | (pyrazole with CH2OMe, methyl, CF3, phenyl-CH2-pyrrolidinone) | 51 | 87.4, 47.4 |
| Example 6 (26) | (pyrazole with CN, methyl, CF3, phenyl-CH2-pyrrolidinone) | 83 | 70.26.2 |
| Example 7 (31) | (pyrazole with CH(OH)-, methyl, CF3, phenyl-CH2-pyrrolidinone) | 66 | 37.7, 31.1 |

| Example (Compound #) | Structure | Mean % response at 40 μM | CLi (μl/min/mg) Rat, human |
|---|---|---|---|
| Comparative Example* | 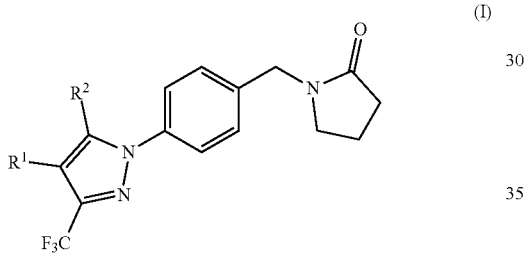 | 7 | 878, 71 |

*The comparative example is the compound disclosed as Example 3 in WO 2008/148836.

NOR Assay

Certain of the exemplified compounds have been tested in the Novel Object Recognition (NOR) assay and exhibit a minimal effective dose of less than 10 mg/kg following oral administration.

The invention claimed is:

1. A compound of the formula (I):

(I)

wherein:
$R^1$ is selected from: $C_{1-4}$ alkyl and $-(CH_2)_aOR^4$, wherein a is an integer selected from 1, 2, 3 and 4, and $R^4$ is H;
$R^2$ is selected from: —CN, $C_{1-4}$ alkyl, cyclopropyl, —$C_{1-4}$ alkylO$C_{1-4}$ alkyl and —$(CR^3R^4)_bOH$;
$R^3$ and $R^4$ are each independently selected from H and $C_{1-4}$ alkyl, provided that at least one $R^3$ or $R^4$ in the —$(CR^3R^4)_bOH$ group is $C_{1-4}$ alkyl; and
b is an integer selected from 1, 2, 3 and 4;
provided that $R^1$ and $R^2$ are not both $C_{1-4}$ alkyl.

2. The compound of claim 1, wherein $R^1$ is selected from: $C_{1-3}$ alkyl and hydroxymethyl.

3. The compound of claim 1, wherein $R^1$ is methyl or hydroxymethyl.

4. The compound of claim 1, wherein $R^2$ is selected from: —CN, $C_{1-3}$ alkyl, cyclopropyl, —$C_{1-2}$ alkylOCH$_3$ and —CH(CH$_3$)OH.

5. The compound of claim 1, wherein $R^2$ is selected from: methyl, ethyl, isopropyl and cyclopropyl.

6. The compound of claim 1, wherein
$R^1$ is selected from $C_{1-3}$ alkyl and hydroxymethyl; and
$R^2$ is selected from —CN, $C_{1-3}$ alkyl, cyclopropyl, —CH(CH$_3$)OH and methoxymethyl;
provided that when $R^1$ is $C_{1-3}$ alkyl then $R^2$ is not $C_{1-3}$ alkyl or cyclopropyl.

7. The compound of claim 1, wherein
$R^1$ is methyl and $R^2$ is selected from: —CN, methoxymethyl and —CH(CH$_3$)OH; or
$R^1$ is hydroxymethyl and $R^2$ is methyl.

8. The compound of claim 1 wherein a and b are independently an integer selected from 1 and 2.

9. The compound of claim 1 selected from:

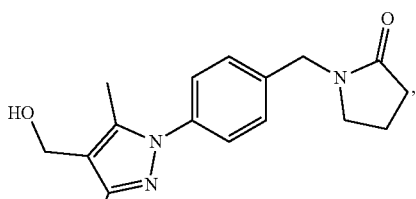

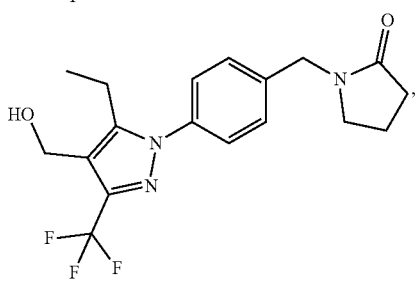

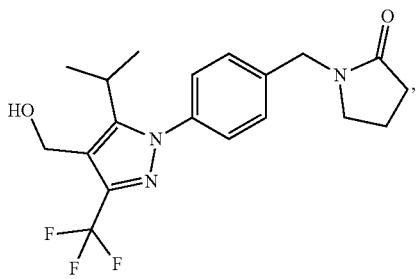

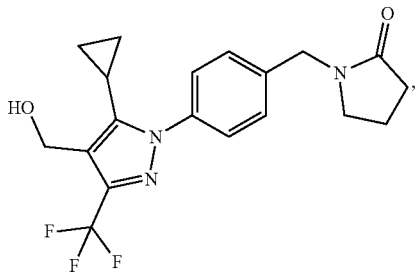

-continued

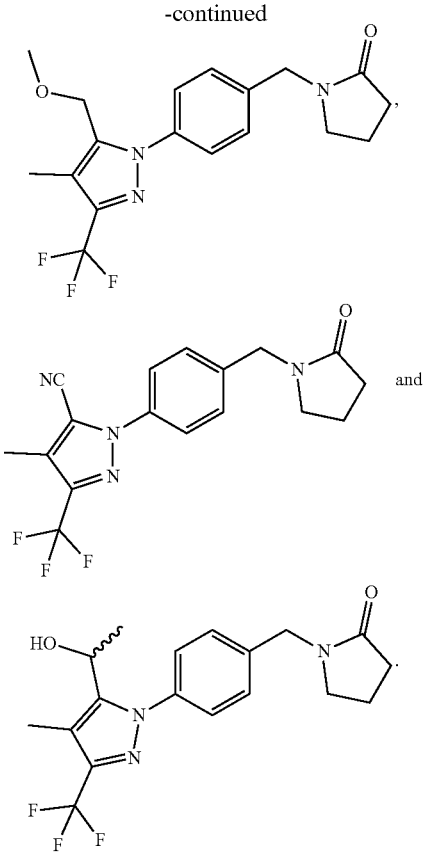

10. A pharmaceutical formulation comprising a compound of claim 1 and a pharmaceutically acceptable excipient.

11. A method for treating a condition which is modulated by an AMPA receptor in a subject in need thereof, the method comprising administering to the subject a therapeutically effective amount of a compound according to claim 1.

12. The method according to claim 11, wherein the compound is co-administered to a subject with an additional therapeutic agent.

13. The method of claim 12, wherein the additional therapeutic agent is selected from an antipsychotic and an anti-depressant.

14. A compound of the formula (IV):

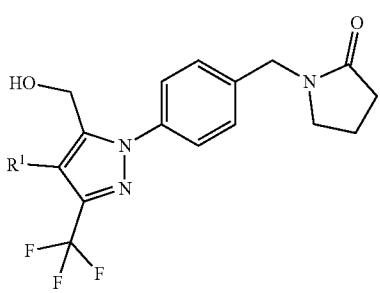

(IV)

wherein $R^1$ is $C_{1-4}$ alkyl.

15. The compound of claim 14, wherein $R^1$ is methyl.

16. The compound of claim 1, wherein $R^2$ is selected from methyl, methoxymethyl, and —CH(CH$_3$)OH.

17. A method for treating a condition modulated by an AMPA receptor in a subject in need thereof, wherein the condition is selected from a depressive disorder, a mood disorder, cognitive dysfunction, a psychotic disorder, a bipolar disorder, attention-deficit hyperactivity disorder, a neurodegenerative disorder, a neurodevelopmental disorder, a motor neuron disease, ataxia, respiratory depression and a hearing disorder in a subject in need thereof, the method comprising administering to the subject a therapeutically effective amount of a compound according to claim 1.

18. The method according to claim 17, wherein the condition is cognitive dysfunction associated with a neurological or neuropsychiatric disorder.

19. The method according to claim 17, wherein the condition is cognitive dysfunction associated with schizophrenia.

20. The method according to claim 17, wherein the compound is co-administered to a subject with an additional therapeutic agent.

* * * * *